(12) United States Patent
Tada et al.

(10) Patent No.: US 10,134,614 B2
(45) Date of Patent: Nov. 20, 2018

(54) SUBSTRATE PERIPHERAL PORTION MEASURING DEVICE, AND SUBSTRATE PERIPHERAL PORTION POLISHING APPARATUS

(71) Applicant: EBARA CORPORATION, Tokyo (JP)

(72) Inventors: Mitsuo Tada, Tokyo (JP); Yasunari Suto, Tokyo (JP); Hirofumi Ichihara, Tokyo (JP); Kenya Ito, Tokyo (JP); Tamami Takahashi, Tokyo (JP)

(73) Assignee: Ebara Corporation, Tokyo (JP)

( * ) Notice: Subject to any disclaimer, the term of this patent is extended or adjusted under 35 U.S.C. 154(b) by 723 days.

(21) Appl. No.: 14/579,292

(22) Filed: Dec. 22, 2014

(65) Prior Publication Data

US 2015/0101752 A1     Apr. 16, 2015

Related U.S. Application Data

(62) Division of application No. 11/596,714, filed as application No. PCT/JP2005/009821 on May 23, 2005, now abandoned.

(30) Foreign Application Priority Data

May 28, 2004    (JP) ................................ 2004-159520

(51) Int. Cl.
 *H01L 21/67*     (2006.01)
 *G01N 29/44*    (2006.01)
 (Continued)

(52) U.S. Cl.
 CPC ........ *H01L 21/67242* (2013.01); *B24B 9/065* (2013.01); *B24B 49/12* (2013.01);
 (Continued)

(58) Field of Classification Search
 None
 See application file for complete search history.

(56) References Cited

U.S. PATENT DOCUMENTS 5,672,091 A    9/1997  Takahashi et al.
6,000,996 A   12/1999  Fujiwara
(Continued)

FOREIGN PATENT DOCUMENTS

EP    1 296 352     3/2003
JP    07-276229    10/1995
(Continued)

OTHER PUBLICATIONS

Machine Generated English Translation of JP2003-139523. Published May 14, 2003.*

(Continued)

*Primary Examiner* — Sylvia MacArthur
(74) *Attorney, Agent, or Firm* — Wenderoth, Lind & Ponack, L.L.P.

(57) ABSTRACT

A projecting/receiving unit (52) projects a laser light to a peripheral portion (30) and receives the reflected light while a liquid is being fed to a substrate (14) and is flowing on the peripheral portion (30). A signal processing controller (54) processes the electric signal of the reflected light to decide the state of the peripheral portion (30). The state of the peripheral portion being polished is monitored. Moreover, the polish end point is detected. A transmission wave other than the laser light may also be used. The peripheral portion (30) may also be enclosed by a passage forming member thereby to form a passage properly. The peripheral portion can be properly measured even in the situation where the liquid is flowing on the substrate peripheral portion.

19 Claims, 26 Drawing Sheets

(51) Int. Cl.
*B24B 9/06* (2006.01)
*B24B 49/12* (2006.01)
*G01N 21/95* (2006.01)

(52) U.S. Cl.
CPC ......... *G01N 21/9501* (2013.01); *G01N 29/44* (2013.01); *H01L 21/67023* (2013.01); *H01L 21/67075* (2013.01)

(56) References Cited

U.S. PATENT DOCUMENTS

| | | | |
|---|---|---|---|
| 6,425,801 | B1 | 7/2002 | Takeishi et al. |
| 6,960,115 | B2 | 11/2005 | Weldon et al. |
| 7,252,575 | B2 | 8/2007 | Kobayashi et al. |
| 2001/0014570 | A1 | 8/2001 | Wenski et al. |
| 2003/0169916 | A1 | 9/2003 | Hayashi et al. |
| 2004/0106363 | A1 | 6/2004 | Ishii et al. |
| 2004/0185751 | A1 | 9/2004 | Nakanishi et al. |
| 2005/0191859 | A1* | 9/2005 | Fujikake ............... B24B 37/013 438/692 |
| 2006/0166606 | A1* | 7/2006 | Kobayashi ............ B24B 37/013 451/6 |
| 2006/0250610 | A1* | 11/2006 | Meeks ................. G01B 11/306 356/237.2 |
| 2008/0274670 | A1* | 11/2008 | Tada ..................... B24B 9/065 451/6 |
| 2015/0101752 | A1* | 4/2015 | Tada ..................... B24B 9/065 156/345.13 |

FOREIGN PATENT DOCUMENTS

| | | |
|---|---|---|
| JP | 2000-046537 | 2/2000 |
| JP | 2000-137074 | 5/2000 |
| JP | 2000-352507 | 12/2000 |
| JP | 2003-139523 | 5/2003 |
| JP | 2003-234314 | 8/2003 |
| WO | 2002/01596 | 1/2003 |

OTHER PUBLICATIONS

Machine Generated English Translation of JP2000-046537. Published Feb. 18, 2000.*
Machine Generated English Translation of JP 07-276229. Published Oct. 24, 1995.*
Supplementary European Search Report dated Oct. 28, 2009 in European Application No. EP 05743290.8, a foreign counterpart of the present application.
Machine generated translation of Kozo et al. JP 07-276229 published Oct. 24, 1995.
Definition of circumference as found in www.m-w.com on Jun. 20, 2010.

* cited by examiner

SUBSTRATE PERIPHERAL PORTION MEASURING DEVICE, AND SUBSTRATE PERIPHERAL PORTION POLISHING APPARATUS

BACKGROUND OF THE INVENTION

Field of the Invention

The present invention relates to a substrate peripheral portion measuring device for measuring the state of the peripheral portion of a substrate. The substrate peripheral portion measuring device belongs to a semiconductor wafer peripheral portion polishing apparatus, for example, and is used to measure the polishing state of the peripheral portion being polished.

Background

As miniaturization and high integration of a semiconductor device advance, management of particles becomes more important. One of major problems in the management of the particles is the dust formation, which is caused by the surface roughness to occur on the circumferential peripheral portion of a semiconductor wafer (or substrate) while the semiconductor device is being manufactured.

In the semiconductor device manufacturing process, flaws or a number of minute needle-shaped projections may be formed at the circumferential peripheral portion of the semiconductor wafer thereby to cause the surface roughness. The needle-shaped projections are broken to produce the particles while the semiconductor wafer is being transferred or processed. These particles lead to a drop in the production yield. Thus, it is necessary to remove the needle-shaped projections from the circumferential peripheral portion of the semiconductor wafer.

In recent years, moreover, there is a tendency that Cu is used as the wiring material for the semiconductor device and that the Low-k material is used as an insulating material. When the Cu formed on the circumferential peripheral portion of the semiconductor wafer sticks to the arm of a transfer robot or a cassette for housing the substrate, the Cu can cause the so-called "cross contamination", in which it diffuses to contaminate the remaining steps. On the other hand, the very fragile Low-k film leaves the circumferential peripheral portion of the substrate during the CMP working treatment thereby to damage or scratch the pattern face. It is, therefore, important to clear the circumferential peripheral portion of the semiconductor wafer of the Cu or Low-k film.

As the pattern of the semiconductor wafer becomes highly dense, the sub-micron contamination is deemed as a problem and highlighted as a serious cause for a defect in the wafer process, although not deemed serious in the prior art. Under this background, it is also important to polish off the film or the like of the wafer peripheral portion.

In the general peripheral portion polishing technique of the prior art, the turning wafer is fed with a liquid such as water. A polishing tool such as a polishing tape is pushed to the peripheral portion thereby to polish the peripheral portion.

The prior art cannot grasp the state of the peripheral portion being polished. Therefore, a total polishing time is determined to manage the polishing process. In order to determine the total polishing time, the sample wafer is subjected at first to a polishing treatment of an initial stage, and the wafer end face is then observed by a camera thereby to examine the flaws left in the defective portion. Then, an additional polishing time necessary for a target finish state is calculated, and the additional polish is performed. The additional polishing time is calculated by using a polishing rate. The additional polish and the subsequent camera observation are repeated to determine the total polishing time. The total polishing time thus obtained is applied to the subsequent wafer polish.

Moreover, a wafer peripheral portion measuring device has also been proposed in the prior art. For example, the measurement device of JP-A-2003-139523 (pages 3 and 4, FIG. 1) illuminates the peripheral portion with a diffusive light to photograph the peripheral portion thereby to detect the defect of the peripheral portion from the photograph.

In case, however, the total polishing time is determined by means of a sample wafer, it takes a remarkably long time to repeat the additional polish and the camera observation. Moreover, the total polishing time required for the practice is different for each wafer. Even if the total polishing time is determined with the sample wafer, the polish may be short or excessive for another wafer so that the process is not stabilized to lower the productivity.

On the other hand, the wafer peripheral portion measuring device of the prior art has failed to consider the measurement in the presence of a liquid such as water. Therefore, the device of the prior art is not suited for the measurement in the peripheral portion polishing apparatus (i.e., in-line) and during the polish (i.e., in situ). If the peripheral portion could be measured during the polish in the polishing apparatus, the peripheral portion polishing process could be properly managed to improve the productivity.

Here, the background art of the invention has been described on the polish of the wafer peripheral portion. A similar background can apply to purposes other than the peripheral portion polish. For example, there is desired a technique for measuring the peripheral portion in the rinsing process.

DISCLOSURE OF THE INVENTION

The present invention has been conceived under the background thus far described and has an object to provide a peripheral portion measuring device for measuring the state of the peripheral portion properly. This state of the peripheral portion typically means the surface roughness due to flaws or minute projections, and means that the material used in the device manufacturing process, such as Cu or a Low-k material as the insulating material sticks to the surface of the circumferential peripheral portion of the substrate or forms a film-shaped substance.

According to the invention, there is provided a substrate peripheral portion measuring device for measuring the state of the peripheral portion of a substrate. The substrate peripheral portion measuring device comprises: a wave transceiver for transmitting a transmission wave to the peripheral portion while a liquid is being fed to the substrate and is flowing on the peripheral portion, and for receiving a reflected wave from the peripheral portion; and a received wave processing unit for processing the signal of the reflected wave to decide the state of the peripheral portion. Thus, according to the invention, the peripheral portion can be properly measured even in the situation where the liquid flows on the peripheral portion.

Here, the liquid is exemplified by water, and the transmission wave is exemplified by a laser light. The kinds of the liquid and the transmission wave may not be limited but be within a measurable range.

In the invention, the peripheral portion of the substrate includes a bevel portion and an edge portion. The bevel portion is the outer circumference of the substrate, and the edge portion is the two side portions of the bevel portion (i.e., the end portions of the surface and the back). The device of the invention may measure the bevel portion, the edge portion or both the bevel portion and the edge portion. Therefore, the later-described peripheral portion treatment includes the treatments of the bevel portion and the edge portion.

The substrate peripheral portion measuring device of the invention preferably comprises a passage forming portion enclosing the peripheral portion for forming a passage to feed the liquid onto the peripheral portion, and the wave transmitting/receiving portion of the wave transceiver is arranged in the passage. By thus providing the passage forming portion, the liquid flow at the peripheral portion can be stabilized to improve the measuring ability.

The wall face of the passage preferably has a wave collecting face shaped to further reflect the reflected wave thereby to collect the reflected wave, and the wave transceiver has a portion at a position, where the reflected wave is collected, for receiving the reflected wave. This configuration causes the wall face of the passage not only to guide the liquid but also to function as the wave collecting face for collecting the reflected waves. As a result, the wave transceiver can receive the reflected light properly thereby to improve the measuring ability.

The device of the invention preferably comprises a liquid removing unit for blowing away the liquid from the peripheral portion, and the wave transceiver transmits the transmission wave to the place where the liquid is blown away by the liquid removing unit. By thus providing the liquid removing unit, the influences of the liquid can be reduced to improve the measurement precision.

The device of the invention preferably comprises a liquid blocking unit enveloping the peripheral portion partially for blocking the arrival of the liquid at the peripheral portion, and the wave transceiver is disposed to transmit/receive the wave through the liquid blocking unit. By thus providing the liquid blocking unit, the influence of the liquid can be reduced to improve the measurement precision.

In the invention, the reflected wave processing unit may decide the state of the peripheral portion on the basis of the relative change of the reflected wave accompanying the change of the substrate. The reflected wave processing unit may decide the state of the peripheral portion on the basis of the time differentiation of the reflected wave accompanying the change of the substrate. The reflected wave processing unit may decide the state of the peripheral portion by performing a frequency analysis of the reflected wave.

In the invention, moreover, the reflected wave processing unit may perform an end point detection of the processing of the peripheral portion. The reflected wave processing unit may monitor the state of the treating procedure of the peripheral portion. The reflected wave processing unit may detect a defect of the peripheral portion. Here in the invention, the peripheral portion treatment includes a polishing treatment and an etching treatment. More specifically, the peripheral portion treatment includes a bevel polishing, an edge polishing, a bevel etching and an edge etching. One treatment may be carried out, and a plurality of treatments may also be carried out.

In the invention, moreover, the wave transceiver may transmit at least one of a laser light, a while light, a microwave, an ultrasonic wave and an alternating magnetic field signal as a transmission wave to the peripheral portion. The typical transmission wave is the laser light.

Moreover, a plurality of the wave transceivers may be arranged along the peripheral portion of the substrate. Moreover, the substrate peripheral portion to be measured may have a silicon nitride film, a silicon oxide film, a poly-silicon film, a barrier film of Ta, TaN, TiN, Ti or the like, or a metal film of Cu, W or the like.

Preferably, the reflected wave processing unit has means for clearing the signal of the reflected wave of noise components. By thus removing the noise components, the signal indicating the state of the peripheral portion can be obtained precisely and stably.

Preferably, the wave transceiver is configured to project a laser light and to receive a reflected light; and a beam size is set according to the movement of the turning wafer. By thus setting the beam size according to the wafer movement, the state of the peripheral portion of the wafer can be precisely measured even if the turning wafer moves to some extent.

Preferably, the device of the invention comprises: a modulation unit for modulating the laser light projected as the transmission wave by the wave transceiver; and a synchronism detecting unit for detecting the reflected light received as the reflected wave by the wave transceiver, in synchronism with the modulation by the modulation unit. By thus performing the modulation of the laser light and the synchronous detection of the reflected light, the measurement sensitivity can be augmented to improve the measuring ability.

Preferably, the wave transceiver is configured to send a plurality of kinds of transmission waves, and the signal processing unit is configured to process a plurality of kinds of reflected waves received by the wave transceiver. Here, a plurality of kinds of the transmission waves are those of at least two kinds of the aforementioned laser light, white light, microwave, ultrasonic wave and alternating magnetic field signal. The kind of transmission wave to be used for the measurement is changed according to the material of the substrate peripheral portion to be measured. Moreover, the kind of transmission wave may be changed as the substrate treatment such as the polish advances. By thus selectively using the plurality of kinds of transmission waves, the proper transmission waves can be used to improve the measuring ability.

Preferably, the reflected wave processing unit decides the state of the peripheral portion on the basis of zone data obtained from reflected waves of measurement zones disposed along the outer circumference of the substrate. Here, the zone data represent the reflected waves of the measurement zones and are an average of the amplitudes of the reflected waves obtained from a plurality of measurement zones. By using the zone data, the state of the substrate peripheral portion can be properly grasped to improve the measuring ability.

Preferably, the reflected wave processing unit decides the state of the peripheral portion by comparing the zone data obtained from the measurement zones. By thus comparing the zone data of the measurement zones, the situation of the peripheral portion can be grasped with reference to the measurement zones. As a result, the state of the substrate peripheral portion can be properly grasped to improve the measuring ability.

Preferably, the reflected wave processing unit decides the state of the peripheral portion on the basis of the reflection according to the material change of the surface of the peripheral portion accompanying the treatment of the substrate. By thus noting the change of the reflection according to the material change of the surface of the peripheral portion, the state of the peripheral portion can be precisely decided to improve the measuring ability.

Preferably, the reflected wave processing unit decides the state of the peripheral portion on the basis of the change of the pattern change of the reflected wave according to the material change of the surface of the peripheral portion accompanying the treatment of the substrate. By thus noting the change of the reflection pattern according to the material change of the surface of the peripheral portion, the state of the peripheral portion can be precisely decided to improve the measuring ability.

Moreover, the measuring device of the invention may belong to a substrate peripheral portion polishing apparatus for polishing the peripheral portion of a substrate, and may measure the polished state of the peripheral portion of the substrate being polished. Moreover, the measuring device may belong to a substrate treating apparatus provided with a substrate peripheral portion polishing apparatus for polishing the peripheral portion of a substrate, and may measure the polished state of the peripheral portion of the substrate being polished.

Moreover, the measuring device may belong to a substrate rinsing apparatus, and may measure the polished state of the peripheral portion of the substrate being rinsed. Moreover, the measuring device may belong to substrate treating apparatus provided with a substrate rinsing apparatus, and may measure the polished state of the peripheral portion of the substrate being rinsed.

According to another aspect of the invention, there is provided a substrate peripheral portion polishing apparatus which comprises: a substrate holder for holding a substrate; a substrate turning unit for turning the substrate; a liquid supply unit for supplying the substrate with a liquid; an peripheral portion polishing unit for polishing the peripheral portion of the substrate while being supplied with the liquid; a wave transceiver for transmitting a transmission wave to the peripheral portion while the liquid is flowing on the peripheral portion, and for receiving a reflected wave from the peripheral portion; a received wave processing unit for processing the signal of the reflected wave to decide the polished state of the peripheral portion; and a control unit for controlling the polish of the peripheral portion in accordance with the polished state of the peripheral portion obtained by the received wave processing unit. Thus, the invention can measure the peripheral portion properly even in the situation where the liquid flows on the peripheral portion. Therefore, the invention can measure the state of the peripheral portion being polished.

Preferably, the substrate peripheral portion polishing apparatus comprises a passage forming portion enclosing the peripheral portion for forming a passage to feed the liquid onto the peripheral portion, and the wave transmitting/receiving portion of the wave transceiver is arranged in the passage. By thus providing the passage forming portion, the flow of the liquid on the peripheral portion can be stabilized to improve the measuring ability.

Preferably, the wall face of the passage has a wave collecting face shaped to further reflect the reflected wave thereby to collect the reflected wave and the wave transceiver has a portion at a position, where the reflected wave is collected, for receiving the reflected wave. This configuration causes the wall face of the passage not only to guide the liquid but also to function as the wave collecting face for collecting the reflected waves. As a result, the quantity of the reflected waves received by the wave transceiver can be augmented to improve the measuring ability.

Preferably, the apparatus comprises a liquid removing unit for blowing away the liquid from the peripheral portion, and the wave transceiver transmits the transmission wave to the place where the liquid is blown away by the liquid removing unit. By thus providing the liquid removing unit, the influence of the liquid can be reduced to improve the measurement precision.

Preferably, the apparatus comprises a liquid blocking unit enveloping the peripheral portion partially for blocking the arrival of the liquid at the peripheral portion, and the wave transceiver is disposed to transmit/receive the wave through the liquid blocking unit. By thus providing the liquid blocking unit, the influence of the liquid can be reduced to improve the measurement precision.

In the apparatus, the received wave processing unit may detect the polish end point of the peripheral portion, and the control unit may end the polish of the peripheral portion when the polish end point of the peripheral portion is detected. Moreover, the received wave processing unit may monitor the state of the polishing procedure of the peripheral portion, and the control unit may control the polishing condition of the peripheral portion in accordance with the state of the polishing procedure of the peripheral portion. The control unit may control at least one of the turning speed of the substrate, the pushing force of the polishing tool to the peripheral portion, the feed movement of the polishing tape, the feed speed of the polishing tape, the relative movement of the polishing head with respect to the substrate, the relative moving speed of the polishing head with respect to the substrate, and the feed rate of the liquid. The polishing condition can be effectively changed by controlling at least one of the turning speed of the substrate, the pushing force of the polishing tool to the peripheral portion, the feed movement of the polishing tape, the feed speed of the polishing tape, the relative movement of the polishing head with respect to the substrate, the relative moving speed of the polishing head with respect to the substrate, and the feed rate of the liquid. Moreover, the received wave processing unit may decide whether or not the peripheral portion is defective.

Preferably, the apparatus comprises an abnormality detecting unit for detecting that a polish abnormality has occurred when the polish end point is not detected even if the polishing time reaches a predetermined maximum polishing time, and the control unit stops the polish when the abnormality is detected by the abnormality detecting unit. As a result, the apparatus can cope with the polish abnormality properly.

Preferably, the apparatus comprises an abnormality detecting unit for detecting that a polish abnormality has occurred when the waveform of the reflected wave is abnormal, and the control unit stops the polish when the abnormality is detected by the abnormality detecting unit. As a result, it is possible to cope with the polish abnormality properly.

Preferably, the apparatus comprises a tool exchange informing unit for informing the arrival of an exchanging timing of a polishing tool when the polishing rate obtained from the reflected wave lowers to a predetermined tool exchanging threshold rate. As a result, the exchanging timing can be properly informed to promote the exchange at a proper timing.

Preferably, the wave transceiver is configured to send a plurality of kinds of transmission waves, and the kind of the transmission wave to be used for the measurement is changed according to the proceeding situation of the polishing procedure determined from the reflected wave. Here, the plurality of kinds of transmission waves are those of at least two kinds of the aforementioned laser light, white light, microwave, ultrasonic wave and alternating magnetic field signal. By thus selectively using the plurality of kinds of transmission waves, the proper transmission waves can be used to improve the measuring ability.

Preferably, the wave transceiver is configured to send a plurality of kinds of transmission waves, and the kind of the transmission wave to be used for the measurement is changed in association with the change of the polishing condition by the control unit. By thus changing the kinds of transmission waves according to the polishing condition, the proper transmission waves can be used to improve the measuring ability.

Preferably, the control unit controls the polish of the substrate on the basis of the polishing state and the control parameter of a peripheral portion polishing tool. Here, the control parameter is exemplified by the torque current of the control motor of the polishing tape. By thus utilizing the control parameter, the polish control can be properly made.

Preferably, the control unit interchanges the control based on the control parameter and the control based on the polishing state, in accordance with the progress of the polishing procedure of the substrate. For example, a coarse control is made in the first half of the polish on the basis of the control parameter, and a fine control is made in the second half of the polish by using the reflected wave. Thus, the polish control can be made by using the control parameter properly.

Preferably, the received wave processing unit detects the polish endpoint by comparing the polish end point target set according to the reflected wave at an initial polishing stage and the reflected wave obtained from the wave transceiver. By setting the polish end point target, the polish end point can be properly detected.

Preferably, the apparatus comprises an end time setting unit for setting the polish end time, at which the polish end point is reached, on the basis of a reference time till a predetermined reference polishing state is obtained in the polishing procedure. As a result, the polishing time can be precisely set by using the information on the polishing state obtained by the measurement during the polish.

According to another aspect of the invention, there is provided a substrate rinsing apparatus, which comprises: a substrate holder for holding a substrate; a substrate turning unit for turning the substrate; a liquid supply unit for supplying the substrate with a liquid; a wave transceiver for transmitting a transmission wave to the peripheral portion of the substrate while the liquid is flowing on the peripheral portion, and for receiving a reflected wave from the peripheral portion; and a received wave processing unit for processing the signal of the reflected wave to decide the polished state of the peripheral portion. Thus, the aspect of the substrate rinsing apparatus can also achieve the advantages of the invention.

According to another aspect of the invention, there is provided a substrate peripheral portion measuring method for measuring the state of the peripheral portion of a substrate. In this method: a transmission wave is transmitted to the peripheral portion while a liquid is being fed to the substrate and is flowing on the peripheral portion; a reflected wave is received from the peripheral portion; and the signal of the reflected wave is processed to decide the state of the peripheral portion. Thus, the mode of the substrate peripheral portion measuring device can also achieve the advantages of the invention.

According to another aspect of the invention, there is provided a substrate peripheral portion polishing method. In this method: a substrate is held; the substrate is turned; the substrate is supplied with a liquid; the peripheral portion of the substrate is polished while the liquid is being supplied; a transmission wave is transmitted to the peripheral portion while the liquid is flowing on the peripheral portion; a reflected wave is received from the peripheral portion; the signal of the reflected wave is processed to decide the polished state of the peripheral portion; and the polish of the peripheral portion is controlled in accordance with the polished state of the peripheral portion.

According to another aspect of the invention, there is provided a substrate peripheral portion rinsing method. In this method: a substrate is held; the substrate is turned; the substrate is supplied with a liquid; a transmission wave is transmitted to the peripheral portion of the substrate while the liquid is flowing on the peripheral portion; a reflected wave is received from the peripheral portion; and the signal of the reflected wave is processed to decide the polished state of the peripheral portion.

According to the invention, as has been described hereinbefore, the peripheral portion can be properly measured even in the situation where the liquid flows at the peripheral portion. For example, the peripheral portion can be properly measured midway of the polish of the peripheral portion of the wafer substrate. By measuring the peripheral portion during the polish, the visual inspection and the polishing time setting work of the prior art can be eliminated to improve the productivity.

DETAILED DESCRIPTION

The following detailed description refers to the accompanying drawings. The following detailed description and the accompanying drawings do not limit the invention. Instead, the scope of the invention is defined by the appended claims.

In the present embodiment, a substrate peripheral portion measuring device belongs to a substrate peripheral portion polishing apparatus for polishing the peripheral portion of a semiconductor wafer.

Figure 1:
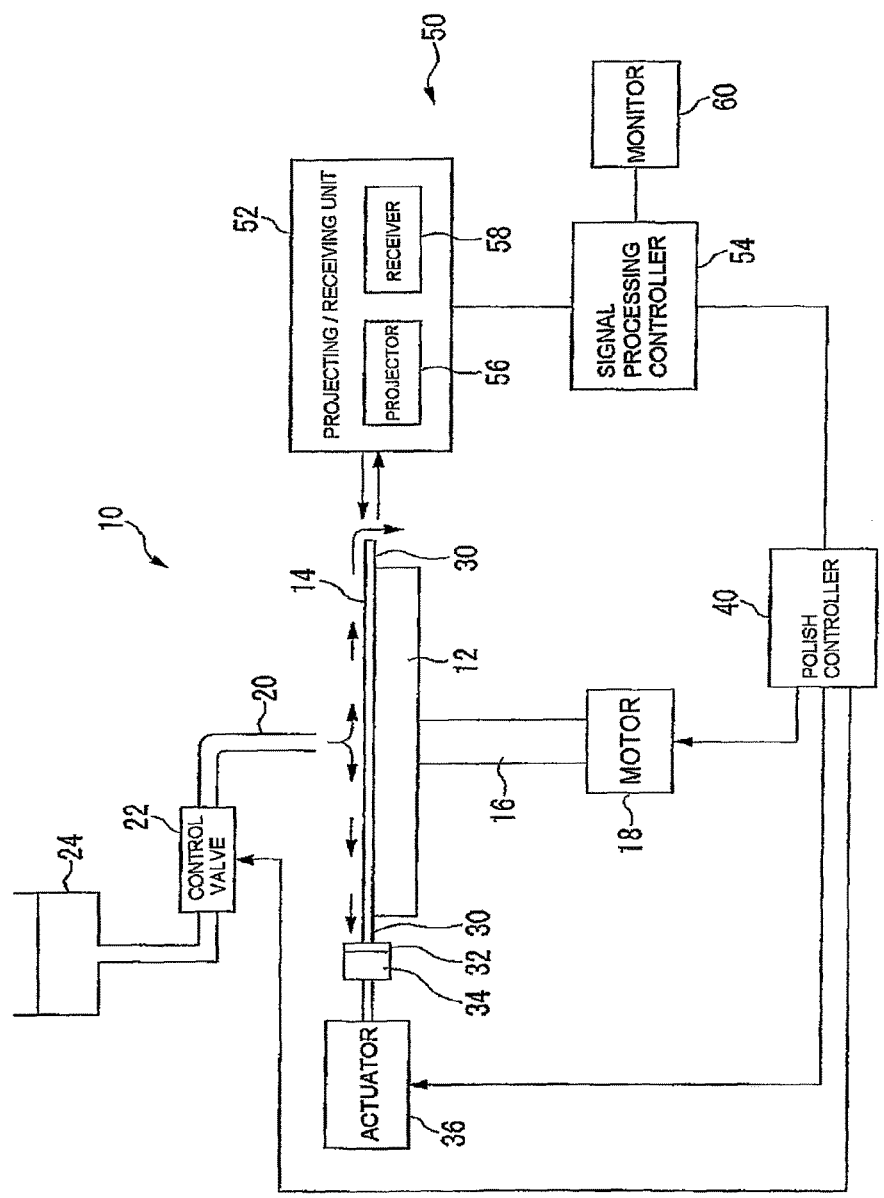
FIG. 1 is a diagram showing a substrate peripheral portion polishing apparatus of an embodiment.

In FIG. 1, a substrate peripheral portion polishing apparatus 10 is provided with a turnable substrate holder 12. A wafer 14 is held on the substrate holder 12. The spindle 16 of the substrate holder 12 is connected to a motor 18. When this motor 18 rotates, the wafer 14 turns with the substrate holder 12. Above the substrate holder 12, there is disposed a nozzle 20. This nozzle 20 is connected through a control valve 22 to a water tank 24.

As a component for polishing the peripheral portion 30 of the wafer 14, there is disposed a polishing tape 32. This polishing tape 32 is a polishing tool having a polishing material adhered to the tape. This polishing tape 32 is arranged to contact with the wafer peripheral portion 30. The polishing tape 32 is backed by a pad 34, which is pushed by an actuator 36. This actuator 36 pushes the pad 34 and then the polishing tape 32 onto the peripheral portion 30 of the wafer 14. The actuator 36 is constructed of a cylinder.

Here in this embodiment, the peripheral portion of the substrate includes a bevel portion and an edge portion. The bevel portion is the outer circumference of the substrate. The edge portion is the two side portions of the bevel portion (i.e., the end portions of the surface and the back).

Figure 1A:
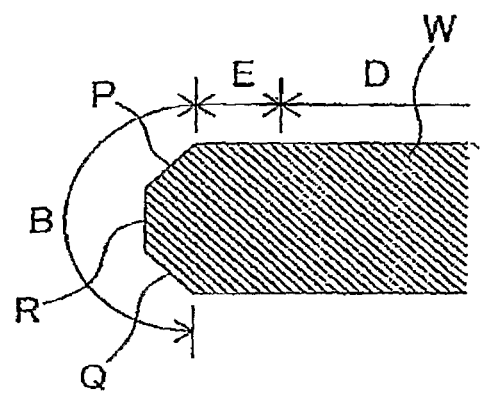
FIG. 1A is a sectional view of a peripheral portion of a straight type wafer.
Figure 1B:
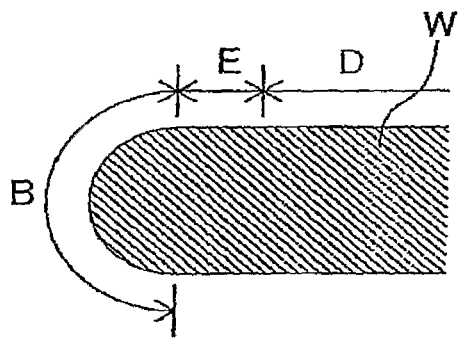
FIG. 1B is a sectional view of a peripheral portion of a round type wafer.

FIG. 1A and FIG. 1B are enlarged sectional views of the portions of the peripheral portions of a wafer. FIG. 1A presents a sectional view of the so-called "straight type" wafer W having a peripheral portion composed of a plurality of straight portions. FIG. 1B presents a sectional view of the so-called "round type" wafer W having a peripheral portion composed of a curved portion. In the following description, the bevel portion of the wafer W of FIG. 1A indicates the portion B. This portion B is composed of upper and lower slopes P and Q sloped from the upper face and lower face of the outer circumference of the wafer W, and a side face portion R of the outer circumference of the wafer W. In the wafer W of FIG. 1B, on the other hand, the bevel portion B of the wafer indicates the portion where the section of the outer circumference of the wafer W has a curvature. Moreover, the edge portion of the wafer indicates the portion of an area E of FIG. 1A and FIG. 1B. This area E is defined by the boundary of the inner side of the bevel portion B of the wafer W and by an upper face D of the wafer W, in which the semiconductor device is to be formed.

In the following description, the peripheral portion of the wafer W includes the bevel portion B and the edge portion E thus specified. In this embodiment, the bevel portion and/or the edge portion may be polished. In the peripheral portion measurement to be described hereinafter, too, the bevel portion and/or the edge portion may also be measured. Here, mainly, the configuration for polishing and measuring the bevel portion is described by way of example.

In this embodiment, the peripheral portion is polished, and this peripheral portion polishing is one peripheral portion treating example. The peripheral portion treatment includes etching. More specifically, the peripheral portion treatment includes a bevel polishing, an edge polishing, a bevel etching and an edge etching. Here is described the polishing treatment.

Reverting to FIG. 1, a polish controller 40 is a computer for controlling the aforementioned substrate peripheral portion polishing apparatus 10 as a whole. The polish controller 40 is configured to control the motor 18, the control valve 22 and the actuator 36.

In the entire peripheral portion polishing actions, the polish controller 40 controls the motor 18 to turn the substrate holder 12 together with the wafer 14. Moreover, the polish controller 40 opens the control valve 22 to feed the (pure) water of the water tank 24 to the upper face of the wafer 14 through the nozzle 20. The water spreads on the upper face of the wafer 14 and flows to the peripheral portion 30, from which it drops. In this state, the polish controller 40 controls the actuator 36 to push the polishing tape 32 to the peripheral portion 30 of the wafer 14. As a result, the polishing tape 32 polishes the peripheral portion 30.

In FIG. 1, the nozzle 20 is located at the center portion of the wafer 14 and is directed just below. However, the position and angle of the nozzle 20 are not limited to those of FIG. 1. The nozzle 20 may also be disposed above the wafer periphery within such a range as can feed water necessary for the polish, for example. Alternatively, the nozzle 20 may be inclined with respect to the wafer 14. Then, the water may also be injected at an angle with respect to the wafer 14.

Figure 2:
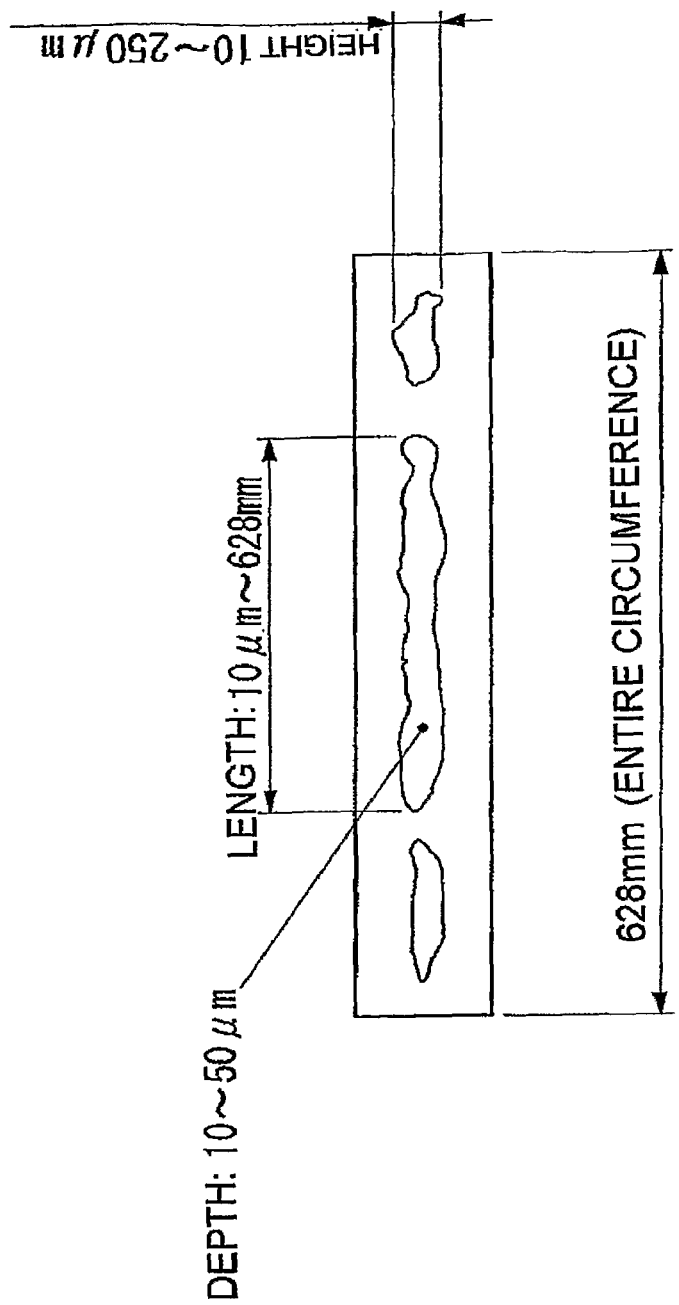
FIG. 2 is a diagram showing an example of flaws of an object to be polished.

On the other hand, FIG. 2 shows an example of flaws of the peripheral portion to be removed in the peripheral portion polishing treatment. In FIG. 2, for example, a wafer of 200 mm has an entire length of a wafer outer circumference of 628 mm. Moreover, the wafer has a flaw height (in the direction of the wafer thickness) of 10 to 250 microns, a length (in the wafer circumference direction) of 10 microns to 628 mm (or the entire length) and a flaw depth of 10 to 50 microns. These flaws are removed by the peripheral portion polishing treatment.

In the peripheral portion polishing treatment, on the other hand, the substrate peripheral portion may have a silicon nitride film, a silicon oxide film ($SiO_2$ (i.e., an oxide film)), a poly-silicon film, a barrier film of Ta, TaN, TiN, Ti or the like, or a metal film of Cu, W or the like. These films are subjected to the following peripheral portion measurement. By removing these films, it is made possible to reduce the adverse affections of the remainder of the film effectively.

Here is described a substrate peripheral portion measuring device 50 which belongs to the substrate peripheral portion polishing apparatus 10. The substrate peripheral portion measuring device 50 is provided with a projecting/receiving unit 52 and a signal processing controller 54. The projecting/receiving unit 52 is provided with a projector 56 and a receiver 58. The projector 56 projects a laser light to the peripheral portion 30 of the wafer 14. The receiver 58 receives the reflected light from the peripheral portion 30. The projection and reception are performed through the film of the water flowing from the peripheral portion 30.

Figure 3:
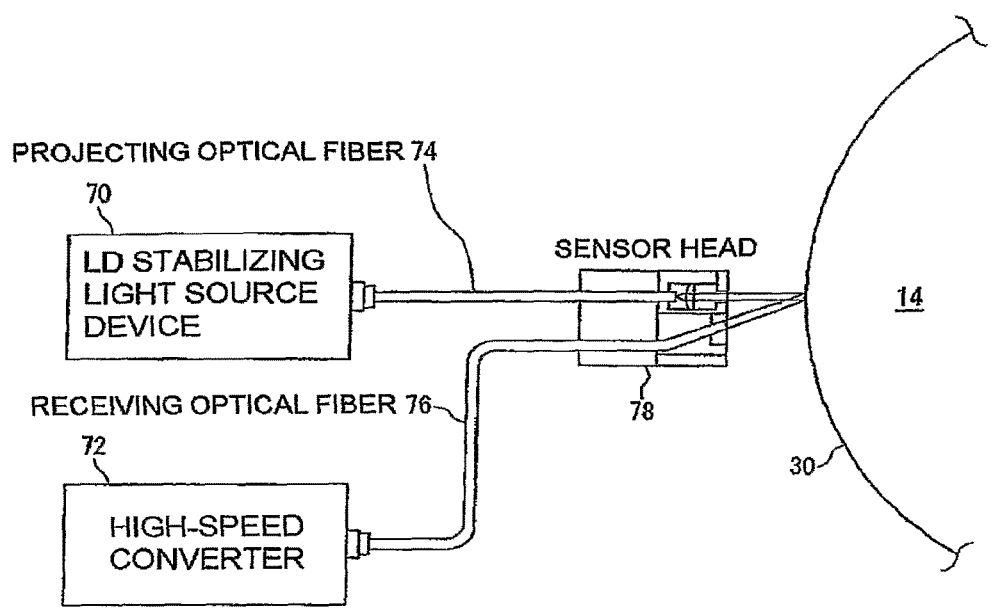
FIG. 3 is a diagram showing a projecting/receiving unit of the substrate peripheral portion measuring device.

FIG. 3 shows a configuration of the projecting/receiving unit 52. In FIG. 3, an LD stabilizing light source device 70 (as will be named the light source device 70) configures the projector, and a high-speed converter 72 (as will be named the converter 72) configures the receiver. A projecting optical fiber 74 is attached to the light source device 70. A receiving optical fiber 76 is attached to the converter 72. The leading ends of the projecting optical fiber 74 and the converter 72 are held in a sensor head 78. The laser light emitted from the light source device 70 passes through the projecting optical fiber 74 and is projected to the wafer 14 through the lens of the sensor head 78. The reflected light from the wafer 14 is received by the receiving optical fiber 76, and reaches the converter 72 through the receiving optical fiber 76. In the converter 72, the optical signal is converted into an electric signal.

Reverting to FIG. 1, the receiver 58 converts the reflected light into the electric signal, as described above, and feeds the electric signal to the signal processing controller 54. This signal processing controller 54 is a computer device, and converts the analog signal of the reflected signal into a digital signal. Moreover, the signal processing controller 54 processes the signal of the reflected light to decide the state of the peripheral portion 30 of the wafer 14. The processed result of the signal processing controller 54 is displayed in a monitor 60 and fed to the polish controller 40.

The signal processing controller 54 may also decide the state of the peripheral portion 30 from the relative change of the effective amplitude of the reflected light. The signal processing controller 54 may further decide the state of the peripheral portion 30 from the time-differential value of the effective amplitude of the reflected light. The signal processing controller 54 may further decide the state of the peripheral portion 30 from the frequency analysis result of the effective amplitude by the FFT analysis. These parameters may be employed in combination.

Moreover, the signal processing controller 54 determines the proceeding situation of the polishing procedure as the state of the peripheral portion 30, and detects a polish end point. At this polish end point, a defect or the like of the peripheral portion 30 is polished away, and the polish should be ended. The signal processing controller 54 may also detect a minute defect in the peripheral portion.

The processed result of the signal processing controller 54 is fed to the polish controller 40, as described above. This polish controller 40 controls the polish on the basis of the state of the peripheral portion 30, which is determined by the signal processing controller 54. In this control, the polish controller 40 controls a polishing condition. The polishing condition is a motor speed, a water feed rate or a polishing tape pushing force. Another polishing condition is a feed of the polishing tape, a feeding speed of the polishing tape, a relative movement of the polishing head with respect to the wafer, or a moving speed of the polishing head relative to the wafer. These parameters may also be controlled. The polishing rate is adjusted by the control of the polishing condition.

When the signal processing controller 54 transmits the detection of the polish end point to the polish controller 40, this polish controller 40 ends the polish. Then, the actuator 36 is controlled so that the polishing tape 32 is brought away from the peripheral portion 30 of the wafer 14. The motor 18 is stopped to stop the rotation of the wafer 14.

[Modifications]

The substrate peripheral portion polishing apparatus 10 and the substrate peripheral portion measuring device 50 of one embodiment of the invention have been described hereinbefore. In this embodiment, the wafer is fed with water. However, the wafer may also be fed with a liquid other than water.

The liquid may be any if it reduces the friction between the polishing tape and the wafer at the polishing time and the heat generation. Alternatively, the liquid or water may be mixed with polishing particles for aiding the polishing ability of the polishing tape. Likewise, the liquid may also be chemicals for aiding in the tape polish either by removing the object by a chemical reaction or by facilitating removal of that.

In the embodiment, on the other hand, the laser light is projected. However, a transmission wave other than the laser light may also be sent. However, a transmission wave other than the laser light may be sent. For example, a white light (of halogen or xenon), a microwave, an ultrasonic wave or an alternating magnetic field signal may be transmitted as the transmission wave. In the case of the halogen white light, the reflected light is condensed for spectroscopic analyses. In the case of the microwave, the reflected light is converted into a signal deflected from the incident signal thereof so that the deflected signal is analyzed. In the type of applying the alternating magnetic field, the reflected magnetic flux from the applied signal is converted into the impedance of an eddy-current sensor so that the converted signal is processed for analyses. In the case of using the microwave, on the other hand, the embodiment is provided with a microwave waveguide. In the case of using the ultrasonic wave, the embodiment is provided with an ultrasonic coaxial cable. In addition, a suitable configuration for wave projections/receptions and for signal processing may also be provided according to the kind of the transmission wave.

In the embodiment, on the other hand, the projecting/receiving unit is disposed at one position on the circumference of the wafer 14. However, the projecting/receiving unit may also be disposed at a plurality of positions. In this case, the state of the peripheral portion 30 is determined with the reflected waves obtained from those positions so that the peripheral portion polish is controlled.

In this embodiment, on the other hand, the sensor head is arranged transversely (with reference to the substrate face) of the wafer 14 so that the projections/receptions are carried out in the transverse direction. On the other hand, the projections/receptions may also be carried out obliquely downward, obliquely upward, downward or upward. Moreover, the projections/receptions may also be carried out in a plurality of directions. For example, the projections/receptions may further be carried out in three directions, obliquely downward, transversely and obliquely upward. The bevel portion and the edge portions above and below the bevel portions can be measured independently of one another.

Here, the aforementioned various modifications can be likewise applied even to the following other embodiments.

In addition, the signal of the reflected light disperses due to the device difference of the projecting/receiving unit, although not explained in the foregoing description. In order to avoid the influence of the dispersion on the measurements, digital amplifications, offsetting and phase processing are properly executed on the sensor hardware unit and its controller. This execution can reduce the influence of the device difference and can improve the measuring precision.

[Passage Formations]

Figure 4:
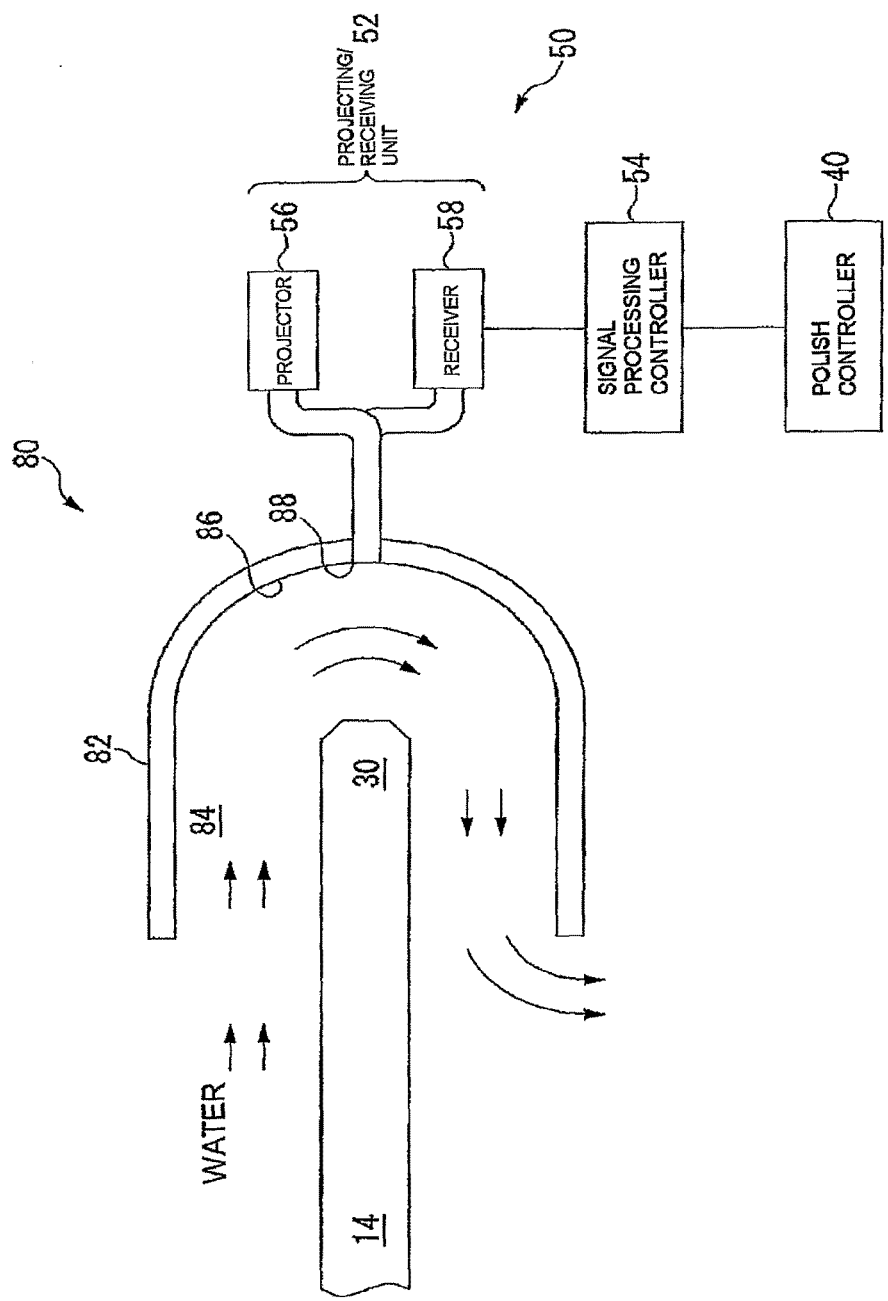
FIG. 4 is a diagram showing a substrate peripheral portion measuring device of another embodiment.
Figure 5:
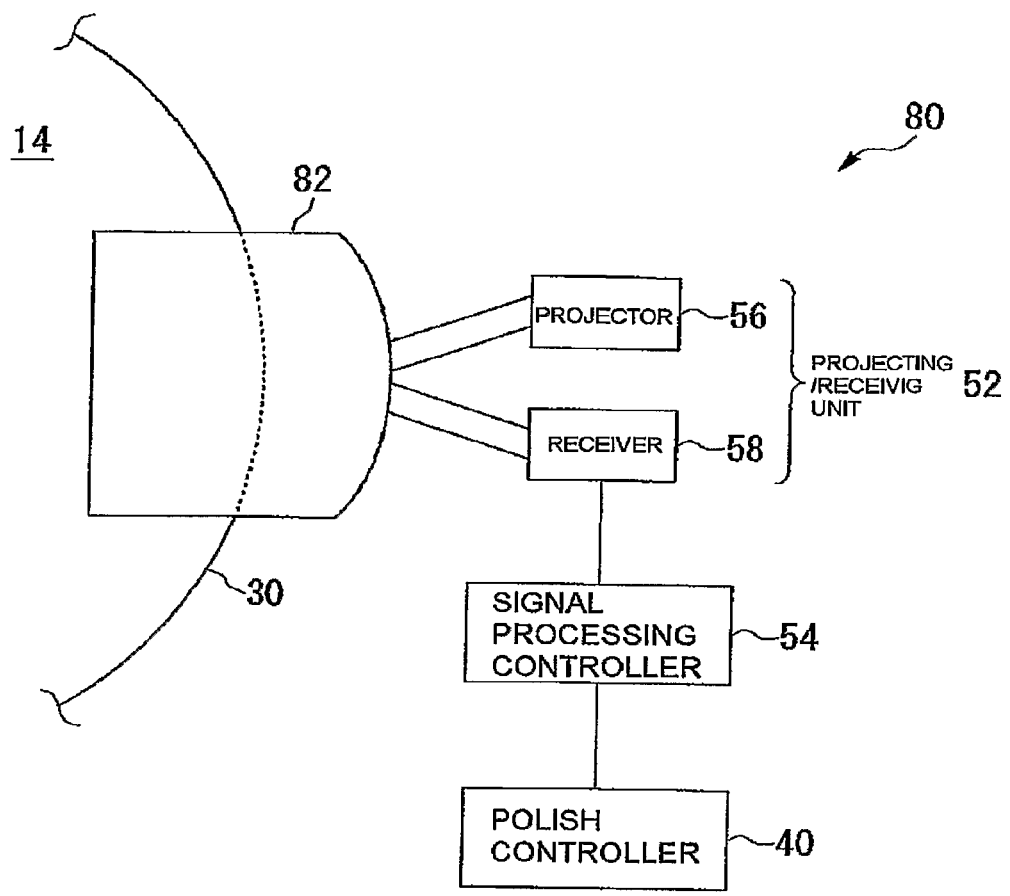
FIG. 5 is a diagram showing a substrate peripheral portion measuring device of another embodiment.

FIG. 4 and FIG. 5 show other configuration examples of the substrate peripheral portion measuring device. As shown, a substrate peripheral portion measuring device 80 is provided with a passage forming member 82 in addition to the aforementioned configuration. This passage forming member 82 has a U-shaped sectional shape. The passage forming member 82 encloses the peripheral portion 30 of the wafer 14 to form a passage 84 for feeding water into the peripheral portion 30. Moreover, the passage forming member 82 is disposed at a portion of the entire wafer circumference. The water is fed from the nozzle 22 to the wafer 14 and flows on the upper face of the wafer 14 and into the passage 84. The water then reaches the peripheral portion 30 in the passage 84 and flows over the peripheral portion 30 and out of the passage 84.

In this embodiment, moreover, the projecting/receiving portions of the projecting/receiving unit 52 are arranged in the passage 84, as shown. More specifically, the (not-shown) sensor head of the projecting/receiving unit 52 is attached to the passage forming member 82. Moreover, the projecting optical fiber and the receiving optical fiber are arranged in a measurement hole 88 formed in the wall face 86 of the passage forming member 82. As a result, the projecting/receiving unit 52 projects the laser light through the water in the passage 84 and receives the reflected light.

Thus in the embodiment, the flow of the liquid at the peripheral portion can be stabilized by providing the passage forming portion. Moreover, the projections/receptions are carried out through the stable flow so that the influence of the flow on the projected/reflected light can be reduced to improve the measuring ability.

[Condensation Face]

Figure 6:
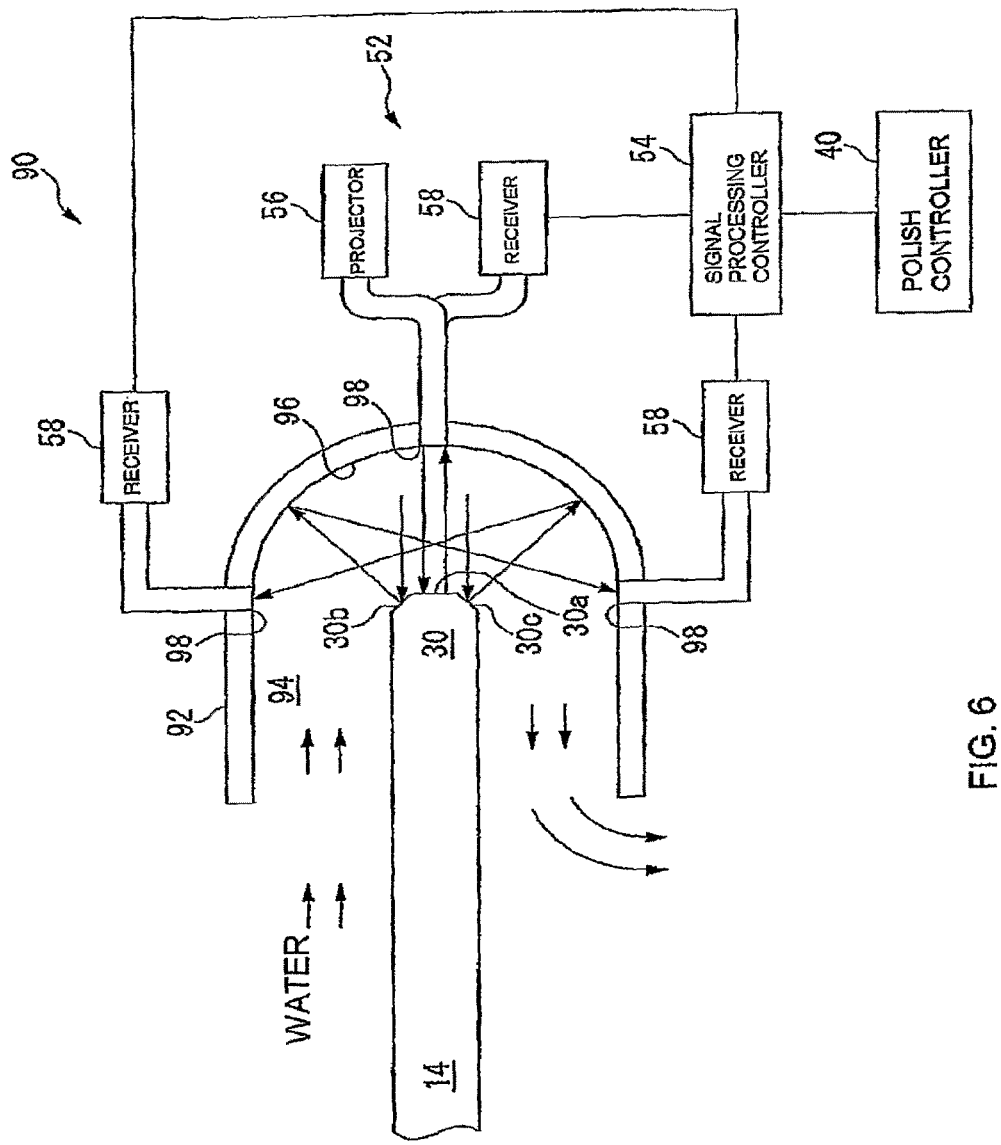
FIG. 6 is a diagram showing a substrate peripheral portion measuring device of another embodiment.

FIG. 6 shows another configuration example of the substrate peripheral portion measuring device. Like the configurations of FIG. 4 and FIG. 5, the substrate peripheral portion measuring device 90 of this embodiment is provided with a passage forming member 92. In this embodiment, moreover, the wall face 96 of the passage 94 of the passage forming member 92 is made of a material for reflecting the laser light. For example, the passage forming member 92 is made of iron or glass having alumina vapor-deposited thereon. As a result, the laser light is reflected on the wall face 96. Moreover, this wall face 96 is made of a wave-collecting face shaped to reflect and collect the reflected light.

More specifically, the peripheral portion 30 of the wafer 14 is composed of a bevel portion 30a and upper and lower corner portions 30b and 30c. The laser light is horizontally projected to the wafer 14. The reflected light of the bevel portion 30a is reflected in a horizontal direction. On the contrary, the reflected light of the upper corner portion 30b proceeds upward and is reflected again on the upper side portion of the wall face 96 so that it is collected downward. On the other hand, the reflected light of the lower corner portion 30c proceeds downward and is reflected again on the lower side portion of the wall face 96 so that it is collected upward.

In this embodiment, as shown, the receiving portion of the reflected light is disposed at the position where the reflected light is collected by the wall face 96. Specifically, the receiving optical fibers are arranged in measuring holes 98 in the upper side portion, the center portion and the lower side portion of the wall face 96. These receiving optical fibers receive the individual reflected lights of the lower corner portion 30c, the bevel portion 30a and the upper corner portion 30b.

Thus, in this embodiment, the passage wall face functions not only to guide the liquid but also as the wave collecting face for collecting the reflected wave. As a result, it is possible to collect the reflected light efficiently.

Here in this embodiment, the condensation may be made within a range so wide as is necessary for satisfying the demand for the measuring ability. The light need not be precisely collected at one point unlike the imaging optical system. Moreover, the condensing unit of the wall face may be a suitable curved face such as a semicircle or semi-ellipse.

[Water Eliminating Configuration]

Figure 7:
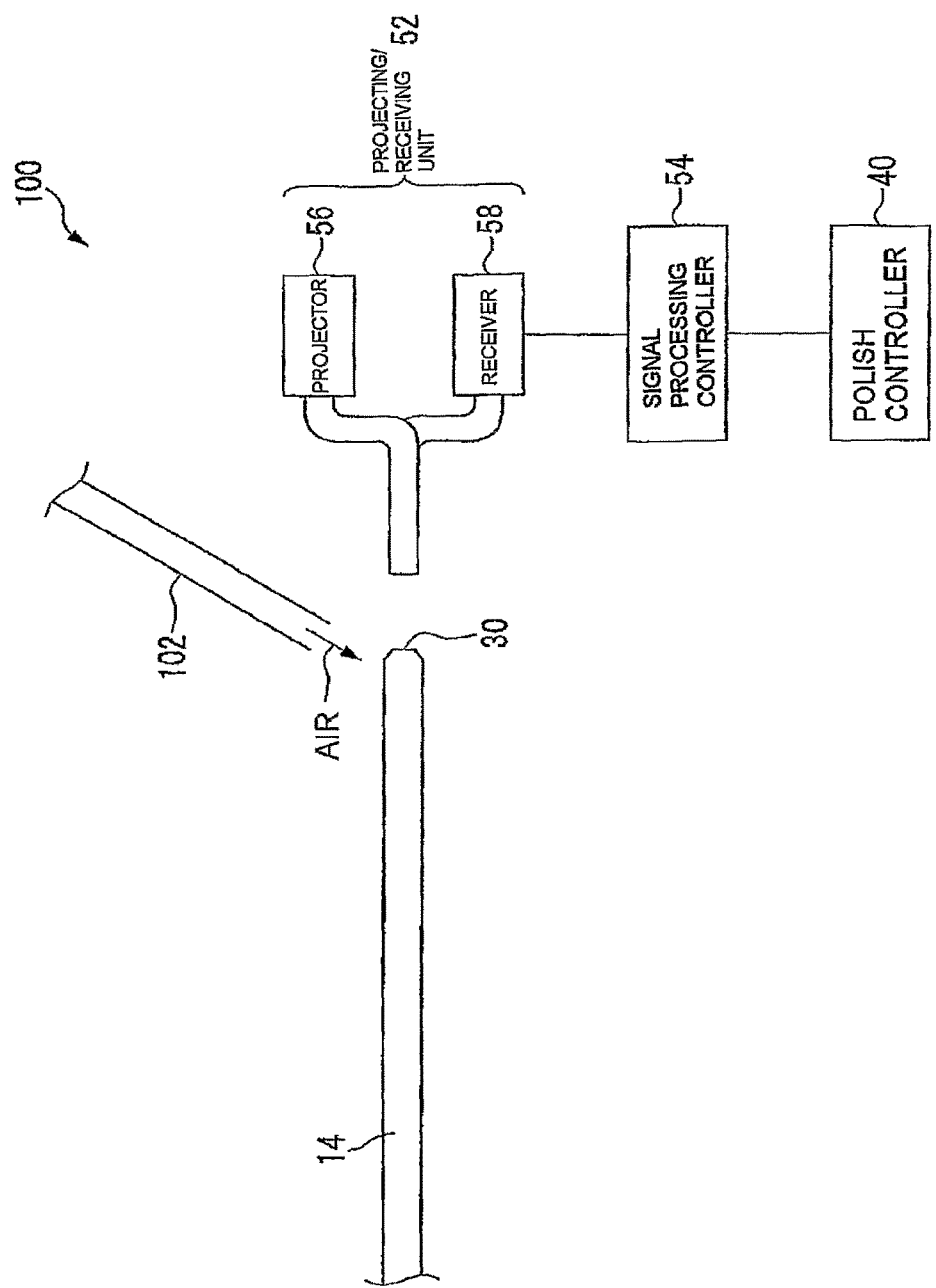
FIG. 7 is a diagram showing a substrate peripheral portion measuring device of another embodiment.
Figure 8:
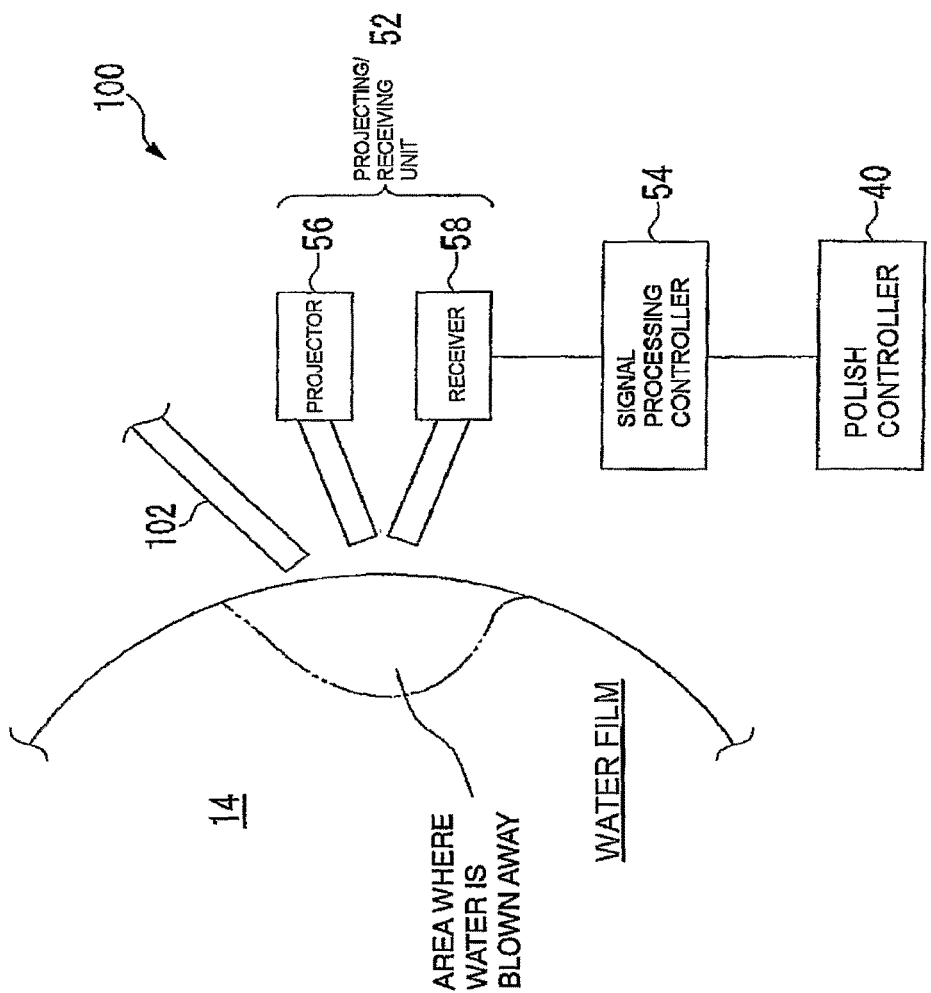
FIG. 8 is a diagram showing a substrate peripheral portion measuring device of another embodiment.

FIG. 7 and FIG. 8 show another configuration example of the substrate peripheral portion measuring device. As shown, the substrate peripheral portion measuring device 100 is provided with a water removing nozzle 102. This water removing nozzle 102 is arranged in the vicinity of the peripheral portion 30 of the wafer 14. The water removing nozzle 102 injects air toward the peripheral portion of the wafer 14 so that it blows off and eliminates the water of the peripheral portion 30 locally.

As shown, the projecting/receiving unit 52 is arranged to project the laser light to the place to be cleared of water. More specifically, the sensor head is arranged in the vicinity of the place to be cleared of water. The projecting optical fiber and the receiving optical fiber project/receive the light to/from the place to be cleared of water.

Thus, this embodiment is provided with the liquid removing unit so that it can reduce the influence of water on the measurements thereby to improve the measuring precision.

Here, the gas to be injected by the water removing nozzle 102 is not limited to air. Specifically, the water removing nozzle 102 may inject a gas other than air, such as a nitrogen gas. The water removing nozzle 102 may inject such a suitable gas, e.g., the nitrogen gas or an inert gas as will not raise the problem that the film on the wafer surface is oxidized or reduced.

[Water Blocking Configuration]

Figure 9:
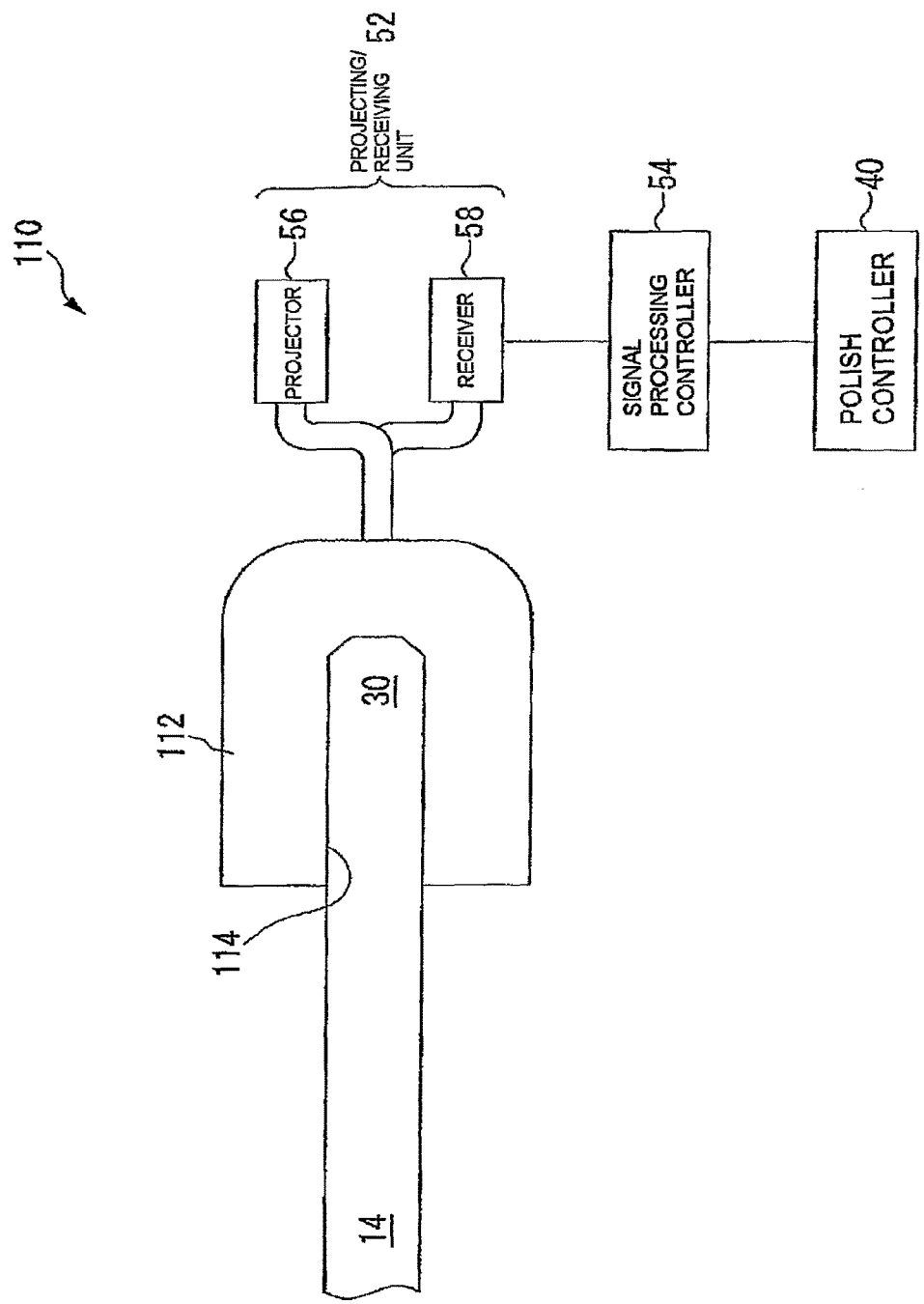
FIG. 9 is a diagram showing a substrate peripheral portion measuring device of another embodiment.
Figure 10:
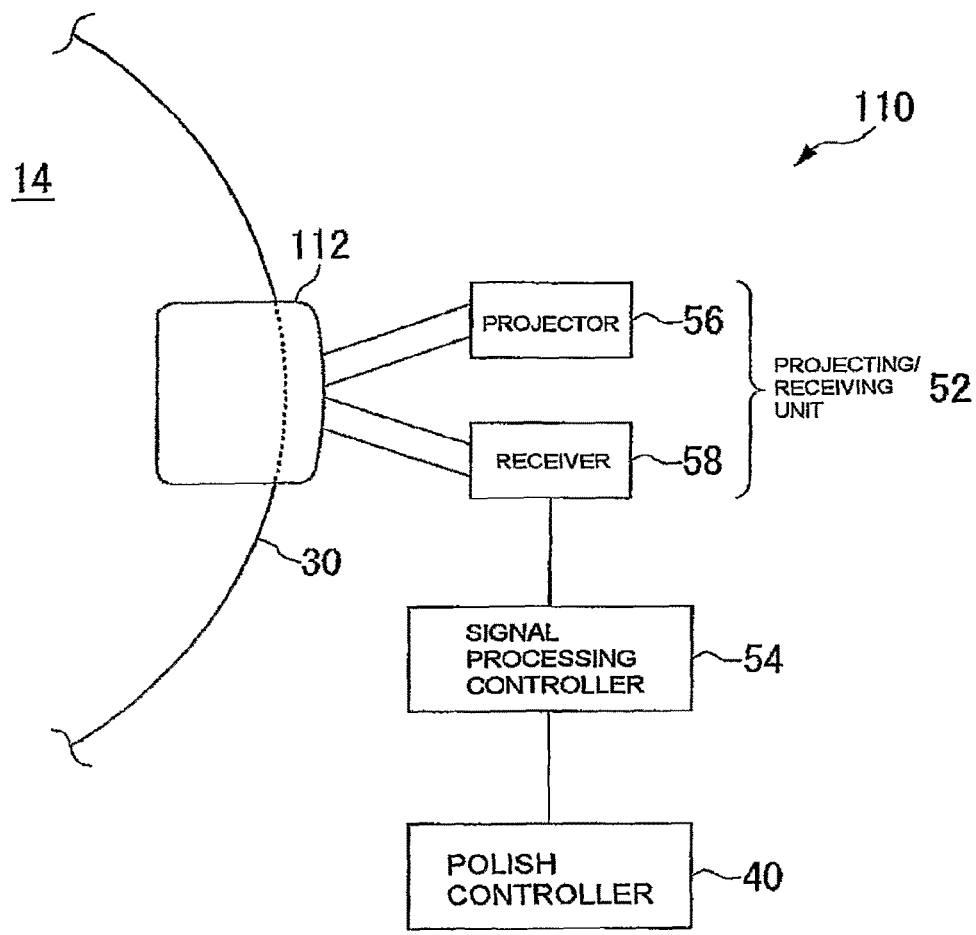
FIG. 10 is a diagram showing a substrate peripheral portion measuring device of another embodiment.

FIG. 9 and FIG. 10 show another configuration example of the substrate peripheral portion measuring device. As shown, the substrate peripheral portion measuring device 110 is provided with a water blocking pad 112. This water blocking pad 112 has a shape for enveloping the peripheral portion 30 of the wafer 14 partially. More specifically, the water blocking pad 112 has a groove 114. The peripheral portion 30 is so fitted in the groove 114 as to closely contact with the inner face of the groove 114. The water blocking pad 112 is fixed. As the wafer 14 turns, therefore, the peripheral portion 30 of the wafer 14 slides in the groove 114.

The water blocking pad 112 is made of such a soft material as not to damage the wafer 14. The water blocking pad 112 is also made of such a transparent material as to transmit the laser light. For example, the water blocking pad 112 is made of a transparent urethane material.

In this embodiment, on the other hand, the projecting/receiving unit 52 is arranged to project/receive the light through the liquid blocking pad 112. More specifically, the sensor head makes contact with the liquid blocking pad 112. The projecting optical fiber and the receiving optical fiber are directed toward the peripheral portion 30 through the liquid blocking pad 112. The optical fibers may bite into the liquid blocking pad 112.

Thus, this embodiment is provided with the liquid blocking unit so that it can reduce the influence of water on the measurements thereby to improve the measuring precision.

[Signal Processing (Real Data)]

Next, the processing of the signal processing controller (54 in FIG. 1) is described in more detail. The signal processing controller converts the analog signal of the reflected light, when it receives the analog signal from the projecting/receiving unit 52, into a digital signal. The signal processing controller processes the signal of the digital type of the reflected light to determine the effective amplitude. Moreover, the signal processing controller determines the state of the peripheral portion 30 from the real data of the effective amplitude. For example, there is determined the relative change of the effective amplitude, from which the proceeding situation of the polishing procedure is monitored to detect the polish end point.

Figure 11:
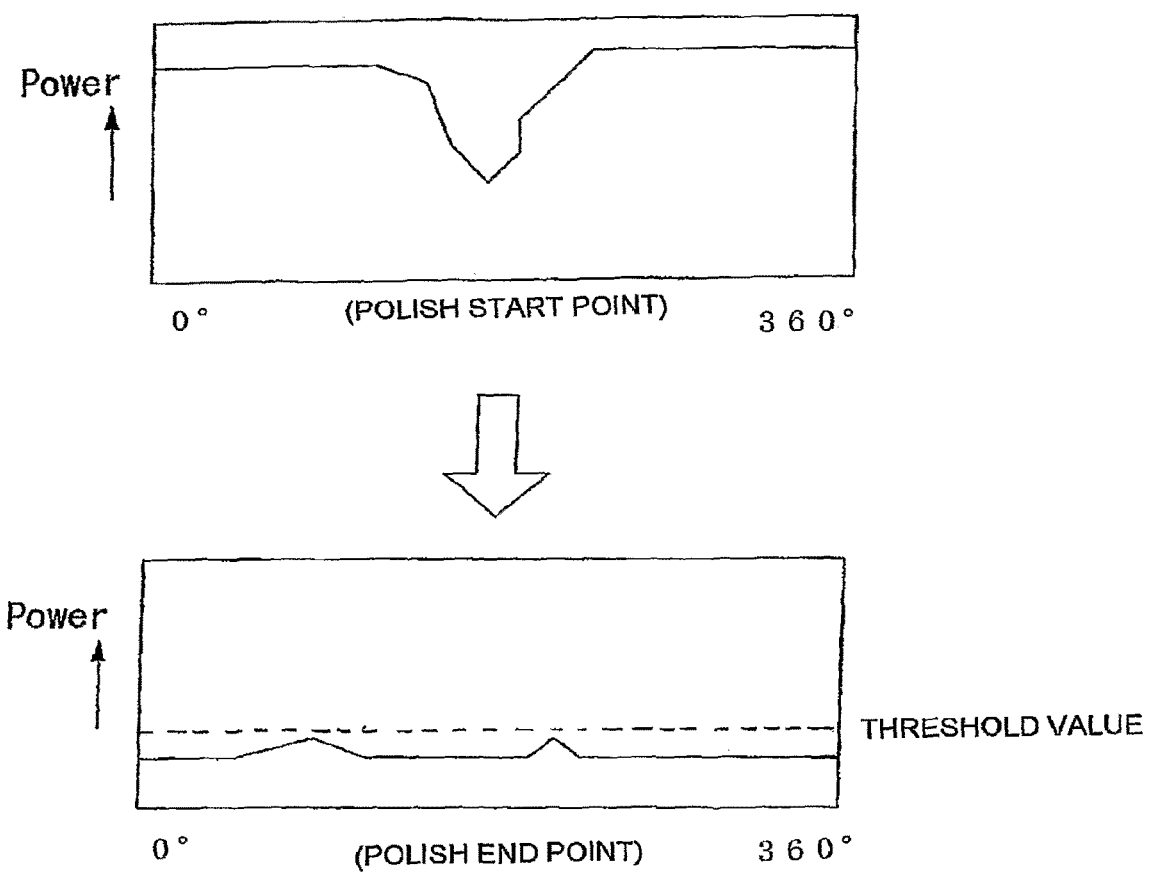
FIG. 11 is a diagram showing a measuring process based on the effective amplitude of a reflected light.

FIG. 11 shows the effective amplitude of the reflected signal schematically. At the polish start time, the amplitude largely changes in a portion on the circumference of the wafer. As the polish proceeds, the peak of the amplitude becomes lower. At the instant when the peak of the amplitude becomes equal to or lower than a predetermined threshold value, the polish end point is detected.

In the example of FIG. 11, the amplitude becomes even as the polish proceeds. However, the amplitude may exhibit a reverse tendency. In this case, the dispersion of the amplitude grows large as the polish proceeds. The polish end point is detected when the dispersion reaches a predetermined threshold value.

Figure 11A:
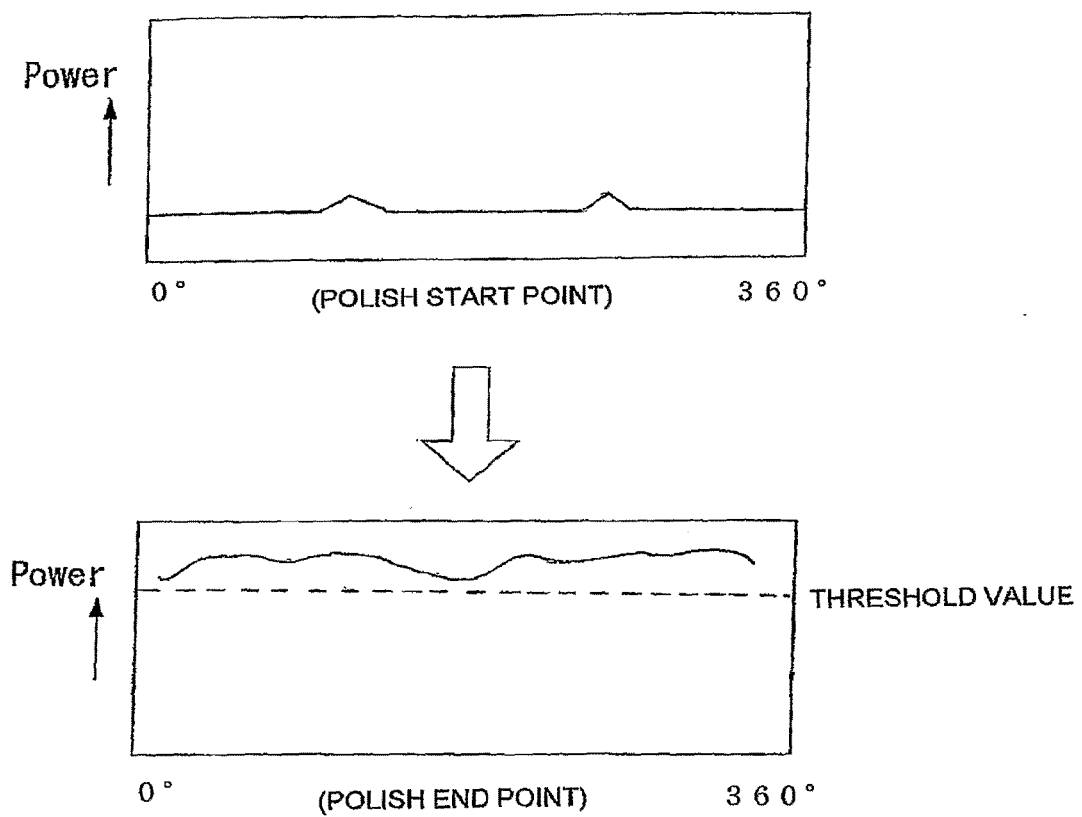
FIG. 11A is a diagram showing a measuring process based on the effective amplitude of a reflected light.

FIG. 11A shows another example. In the example of FIG. 11A, the effective amplitude becomes large as the polish proceeds. The polish end point is detected at the instant when the entire effective amplitude exceeds the threshold value.

The processing of the real data is not limited to the aforementioned examples. An arbitrary featuring event (or a characteristic detected pattern) corresponding to the polish end point may be specified from the real data so that the polish end point may be detected. The usable characteristic event is exemplified by: (1) a value no less than a predetermined value; (2) a value no more than a predetermined value; (3) a maximum; (4) a minimum; (5) a rise start point; (6) a rise end point; (7) a fall start point; (8) a fall end point; (9) a value within a predetermined gradient range; (10) a gradient maximum; or (11) a gradient minimum. A suitable pattern may be used according to the kind of the wafer, the state of the wafer peripheral portion or a measurement target.

[Signal Processing (Time Differentiation)]

On the other hand, the signal processing controller may determine the time differentiation of the effective amplitude thereby to determine the state of the peripheral portion from the time differentiation. In this time differentiation, the polishing situation is grasped from the time differentiation. For example, a pattern corresponding to a flaw is monitored. The polish end point is detected when the flaw pattern disappears.

For the time differentiation, like the real data, the characteristic event corresponding to the polish end time may be extracted from the actually obtained time-differentiated data so that the polish end point may be detected. The examples of the characteristic event are enumerated above.

Here, the time differentiation may be of a first degree, a second degree or a more degree. Differentiations of a plurality of degrees may be used together.

[Signal Processing (Frequency Analysis)]

The signal processing controller may also subject the effective amplitude to the FFT processing for the frequency analysis. In this case, the proceeding situation of the polishing procedure is monitored from the frequency analysis result to detect the polish end point.

Figure 12:
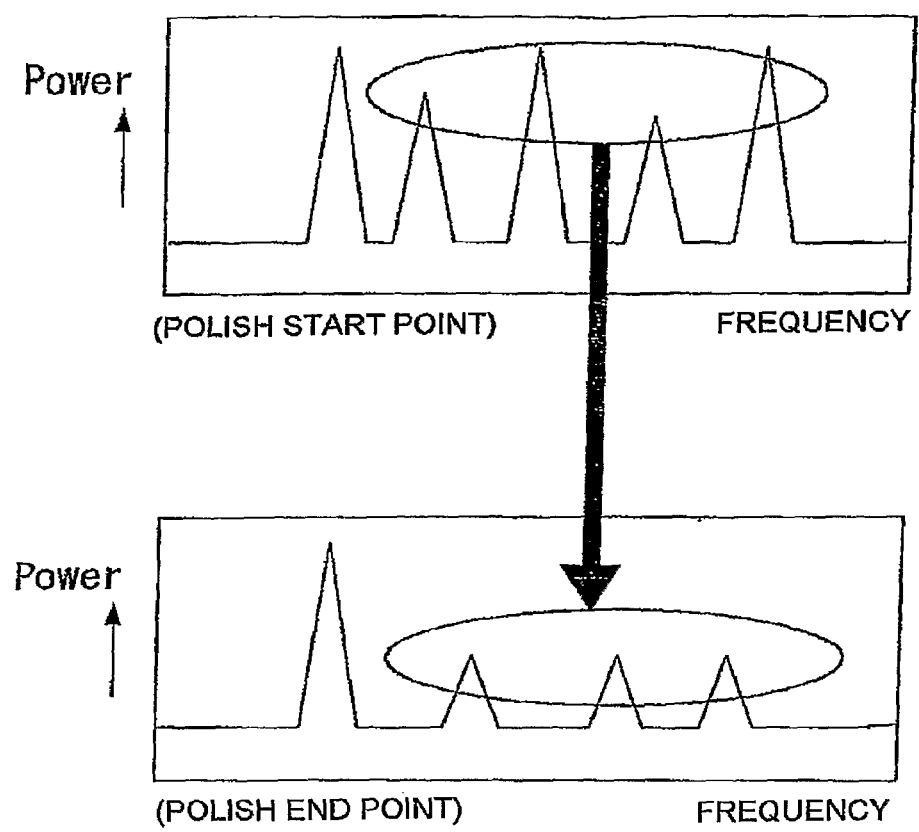
FIG. 12 is a diagram showing a measuring process based on the frequency analyzing result of a reflected light.

FIG. 12 shows one example of the frequency analysis result schematically. In this example, the level of a frequency (e.g., a left-hand peak) is kept as the polish proceeds, but the level of another frequency (e.g., three right-hand peaks) lowers as the polish proceeds. Therefore, the polishing procedure is monitored on the basis of the latter frequency. The polish end point is detected at the instant when the level of the noted frequency lowers to a predetermined threshold level.

In the example of FIG. 12, the levels of some frequencies drop as the polish proceeds. As the polish proceeds, on the contrary, the levels of some frequencies can rise. Moreover, the levels of all frequencies can also rise. In these cases, the state of the peripheral portion can be likewise detected from the result of the frequency analysis.

[Signal Processing (Integration)]

On the other hand, the signal processing controller may also perform a processing to integrate the effective amplitude. In this case, the signal processing controller integrates the signals of the reflected wave, which are obtained along the wafer circumference as the wafer turns. From the integration result, the polished state is determined, and the polish end point is detected. In this case, too, the characteristic event corresponding to the polish end point is extracted from the integration result.

[Signal Processing/Defect Detection]

In the foregoing various processing operations, the polishing procedure is monitored, and the polish endpoint is detected. In addition, the signal processing controller may also detect a defect. Preferably, a characteristic portion indicating a minute defect is extracted from the signal of a reflected wave. The characteristic portion of the minute defect may be extracted from any of the aforementioned real data, the time differentiation, the frequency analysis result or the integration result. A signal indicating the defect occurrence is displayed in the monitor.

Preferably, the signal processing controller acquires the reference (or position) of the wafer from the notch of the wafer, the orientation flat and the signal difference of the remaining portions. Moreover, the signal processing controller acquires information on the turning angle of the wafer. This turning angle of the wafer may be acquired from the angle of rotation of the motor. Moreover, the signal processing controller determines the position of a defect on the basis of the turning angle of the wafer. The position of the defect is expressed by that on the wafer circumference. The position of the defect is also displayed as a portion of the defect information in the monitor.

[Signal Processing/Noise Elimination]

The signal processing controller is configured to eliminate noise components from the signal of the reflected light. For example, the signal processing controller determines the noise components by the FFT signal analysis. In accordance with the noise components specified, the signal processing controller sets the cut-off frequency of a noise eliminating filter. The adjustment of the cut-off frequency is suitably made in the setting of the recipe of a control unit. The filter is exemplified by an LPF (Low Pass Filter), a BPF (Band Pass Filter), an HPF (High Pass Filter) or a notch filter. Filters of a plurality of kinds may also be used together. The filter may also be realized by an analog circuit or by a digital processing.

By thus eliminating the noise components, it is possible to acquire the signal indicating the state of the peripheral portion precisely and stably, to specify the state of the peripheral portion precisely and to detect the polish end point precisely.

[Setting of Beam Size]

Here in this embodiment, the beam size of the laser light is set in the following manner. The wafer moves to some extent in the horizontal direction and in the vertical direction while it is turning. In order that the detection sensitivity may not lower even with the movement of the wafer, the beam size is set according to the movement of the work. As a result, the laser light is converged within the moving range of the work. In other words, the laser light irradiates the peripheral portion of the work properly, even if the work moves within that moving range. The beam size is adjusted by the control for focusing the light source.

In case a minute defect is to be detected, for example, the beam size is set to 10 microns×1,000 microns. The figure of 10 microns is a transverse beam size, and the figure of 1,000 microns is a longitudinal (i.e., the direction of the wafer thickness) beam size. By applying these beam sizes, the defect can be detected even if the wafer moves up and down. Moreover, the transverse beam size is made small, the quantity of light increases to retain the sensitivity for detecting the minute defect.

When the homogeneity of the surface of the wafer peripheral portion is to be measured, for example, the beam is made circular to have a beam diameter of 1 to 2 mm. As a result, the measurement of the entire peripheral portion can be effectively made even if the wafer moves. Because of the homogeneity measurement, moreover, a sufficient performance can be attained even for the large beam size.

Thus in this embodiment, the state of the peripheral portion of the wafer can be precisely measured by setting the beam size according to the movement of the wafer, even if the wafer moves to some extent while it is turning.

[Modulation of Laser Light]

In this embodiment, on the other hand, the laser light is properly modulated, as described in the following.

Figure 13:
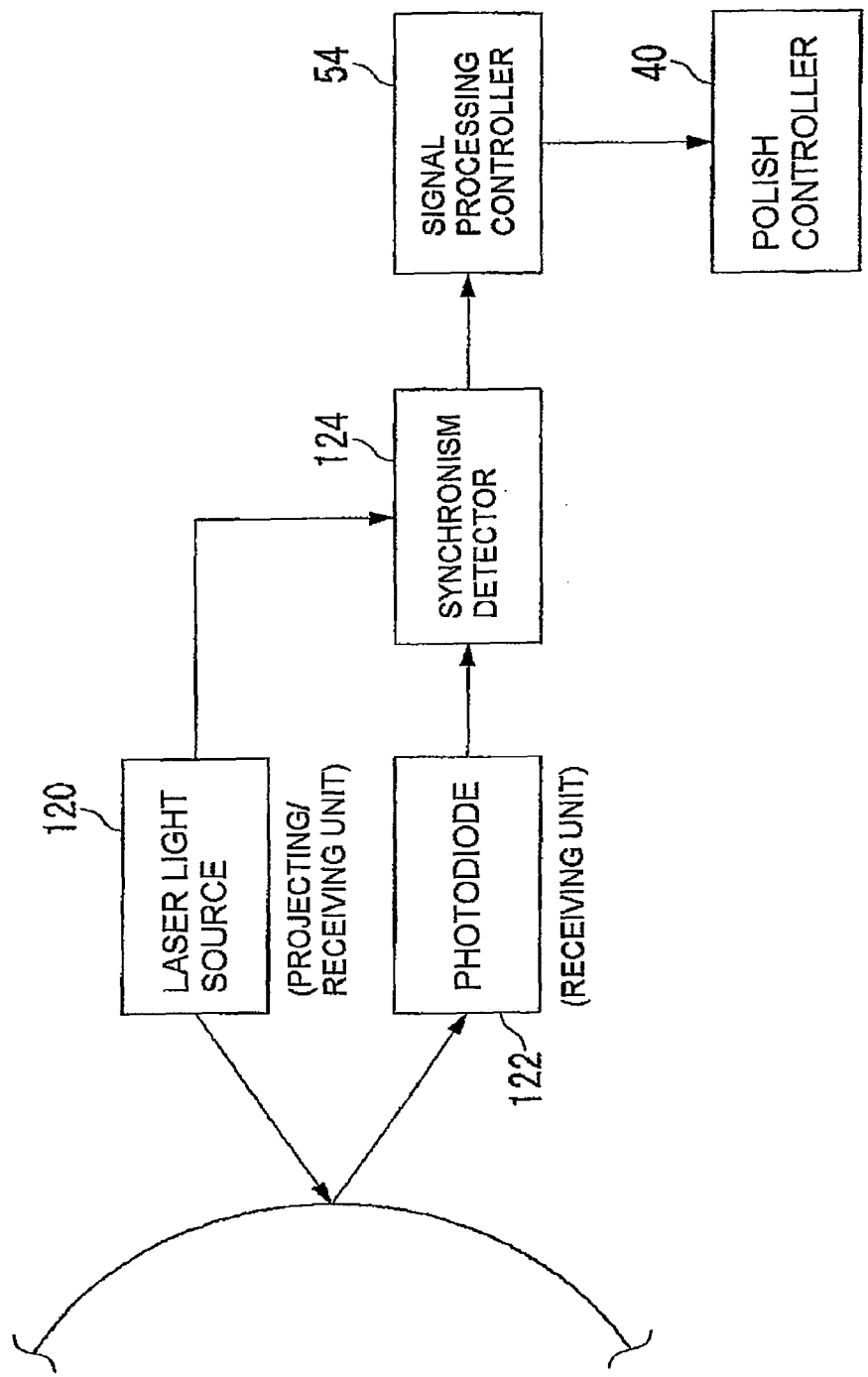
FIG. 13 is a diagram showing a configuration of the case, in which a laser light is modulated.

With reference to FIG. 13, in this embodiment, a pulse modulation is carried out in a laser light source 120. For example, a coherence light source is used, and a pulse modulation of 34 kHz is carried out (although not limited to 34 kHz). As a result, a pulsating laser light is projected on the wafer. A photodiode 122 also receives a pulsating reflected light. The photodiode 122 converts the reflected light into an electric signal. This electric signal is fed to a synchronism detector 124. This synchronism detector 124 is fed with information on the modulation from the laser light source 120. The synchronism detector 124 subjects the signal of the reflected light to a synchronous detection. The synchronously detected signal is fed to the signal processing controller 54.

Thus, this embodiment modulates the laser light. The laser light is modulated, and only the peripheral portion polishing signal is highly sensitively extracted while eliminating the remaining noise signals, thereby to raise the S/N ratio. As a result, the measurement sensitivity can be augmented to improve the measuring ability.

[Polish Control]

Next, the polish control based on the measurement result of the peripheral portion is described in more detail. This control is made by the polish controller (40 of FIG. 1).

The polish controller controls the substrate peripheral portion polishing apparatus, when the polish end point is detected, to end the polish, as has already been described.

During the polish, the polish controller also controls the polishing actions of the substrate peripheral portion polishing apparatus in accordance with the peripheral portion measurement result. Here is carried out the closed loop control.

The object of the control is the wafer turning motor, the water feeding control valve, and the polishing tape pushing actuator. The polish controller controls at least one of the turning speed of the wafer, the pushing force of the polishing tool to the peripheral portion, the feed movement of the polishing tape, the feed speed of the polishing tape, the relative movement of the polishing head with respect to the substrate, the relative moving speed of the polishing head with respect to the wafer, and the feed rate of water. By this control, the polishing speed (or the polishing rate) is adjusted. When the motor speed is raised, for example, the polishing speed is raised. When the tape pushing force is raised, moreover, the polishing speed is raised. These factors may be simultaneously controlled in association. Alternatively, the factors may also be controlled only partially.

Figure 14:
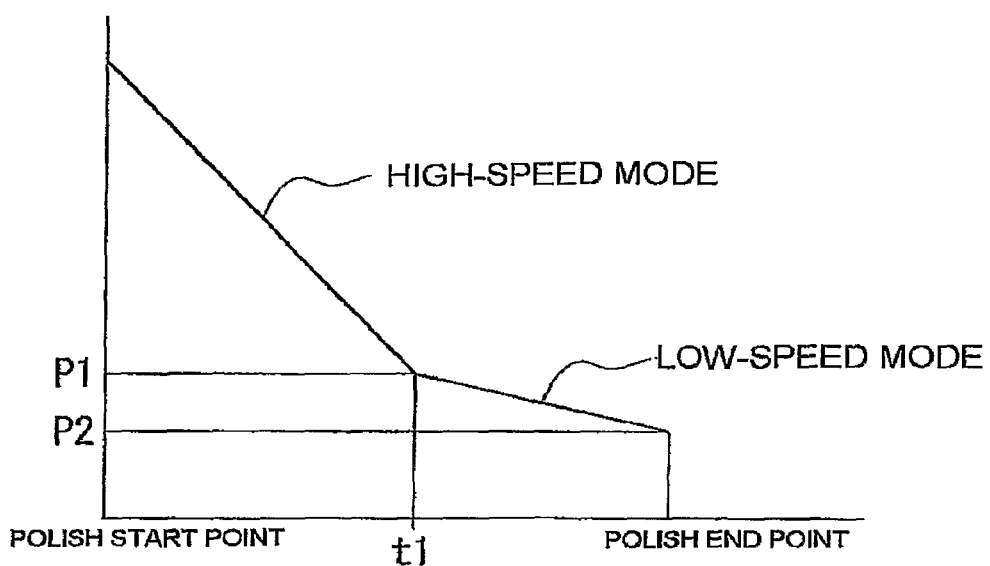
FIG. 14 is a diagram showing a control process of a polishing condition.

FIG. 14 shows an example of a preferable polish control. It is assumed that the peripheral portion polish is performed to expose the silicon film of the wafer to the outside and to smoothen the peripheral portion surface. In FIG. 14, the abscissa indicates the time, and the ordinate indicates a parameter of the polishing state. This parameter is exemplified by the range (i.e., the difference between the maximum and the minimum) of the effective amplitude of the reflected light.

The polish controller causes the polish in a high-speed mode till the parameter of the polishing state reaches a predetermined value P1. Specifically, the motor and so on are controlled so that the polishing speed may take a predetermined high value. When the parameter reaches the value P1 at a time t1, the polishing speed is switched to a low-speed mode for the polish. The motor and so on are controlled so that the polishing speed may take a predetermined value lower than the high-speed mode. When the parameter of the polishing state reaches a value P2 corresponding to the polish end point, the polish controller ends the polish. At this time, the peripheral portion of the wafer is cleared of the unnecessary film or the like so that the silicon face appears with a smooth surface.

Thus, this embodiment can control the polish properly on the basis of the measured state of the peripheral portion. Moreover, the polishing condition can be effectively changed by controlling at least one of the turning speed of the substrate, the pushing force of the polishing tool to the peripheral portion, the feed movement of the polishing tape, the feed speed of the polishing tape, the relative movement of the polishing head with respect to the substrate, the relative moving speed of the polishing head with respect to the substrate, and the feed rate of a liquid. Moreover, the polishing speed can be raised within a proper range on the basis of the measurement result thereby to shorten the polishing time period.

[Abnormality Detection (Excess of Polishing Time)]

Here is described an abnormality detecting function of this embodiment. This function is realized by the signal processing controller 54 of FIG. 1. This signal processing controller 54 receives the information of the polish start from the polish controller 40, and monitors the lapse time from the polish start. The signal processing controller 54 decides whether or not a predetermined maximum polishing time period has elapsed from the polish start. This maximum polish time is preset and stored in the signal processing controller 54.

In case the polish is being normally carried out, the polish end point is detected before the maximum polishing time period elapses. In case the polish end point is not detected even if the maximum polishing time period elapses, it is deemed that some abnormality has occurred. This abnormality can be exemplified by a trouble in the polishing apparatus or in the measuring device.

The signal processing controller 54 decides that a polishing abnormality has occurred, if the polish end point is not detected even when the polishing time period reached the maximum polishing time. The signal processing controller 54 sends a signal indicating the occurrence of an abnormality to the polish controller 40. This polish controller 40 controls the motor and so on, when it receives the signal indicating the abnormality occurrence, to stop the polish forcibly. On the other hand, the signal processing controller displays the abnormality occurrence on the monitor 60.

Thus, according to this embodiment, the polishing abnormality can be properly coped with.

[Abnormality Detection (Abnormality Signal)]

Here is described another abnormality detecting function. In this detecting function, the signal processing controller 54 decides that the polishing abnormality has occurred, if the signal waveform of the reflected light is abnormal. In this processing, the signal processing controller 54 is stored with the information indicating the standard state of the signal waveform of the reflected light. The signal processing controller 54 decides whether or not the waveform of the reflected light obtained by the measurement has deviated from the standard state. When the actual waveform deviates the standard state, the signal processing controller 54 decides that the abnormality has occurred.

The abnormality occurrence is displayed in the monitor 60 and transmitted to the polish controller 40. This polish controller 40 controls the motor and so on to stop the polish forcibly.

Thus, this embodiment can cope with the polishing abnormality properly.

Here have been described the abnormality detections of two kinds (i.e., the abnormality detection due to the excess of the polishing time period, and the abnormality detection due to the abnormal signal). These abnormality detections may be separately used according to the state of the wafer peripheral portion of the object to be measured. One of abnormality detections may also be made according to the state of the wafer peripheral portion.

[Report of Timing for Tool Exchange]

Here is described a function to report the time for a tool exchange in this embodiment. This function is realized by the signal processing controller 54. The signal processing controller 54 monitors the polishing rate obtained from the information on the reflected wave. Here, the signal processing controller 54 receives the information on the polish start from the polish controller 40. On the other hand, the signal processing controller 54 detects the polish end point from the signal of the reflected wave. Moreover, the signal processing controller 54 calculates the polishing rate from the time period from the polish start to the polish end point.

The signal processing controller 54 monitors the polishing rate thus obtained. The polishing rate lowers as a number of wafers are treated. The signal processing controller 54 reports the arrival of the exchanging time of the polishing tool, when the polishing rate drops to a predetermined tool exchanging threshold rate. Here, the signal processing controller 54 displays an image indicating the tool exchanging timing on the monitor 60.

Thus, according to this embodiment, the exchanging timing can be properly reported to promote the exchange of the tool at a proper timing.

In this embodiment, the polishing time period may also be monitored. This polishing time period corresponds to the polishing rate so that the polishing rate can also be monitored by monitoring the polishing time period.

In case the polishing condition is adjusted by the polish controller, it is preferred to monitor the change in the polishing rate in consideration of the polishing condition.

[Combination of Transmission Waves of a Plurality of Kinds]

Here is described a preferred configuration example for combining transmission waves of a plurality of kinds. In the description thus far made, the transmission wave is mainly the laser light. In this embodiment, on the contrary, the transmission waves of a plurality of kinds are combined. One of these transmission waves may naturally be the laser light.

Figure 15:
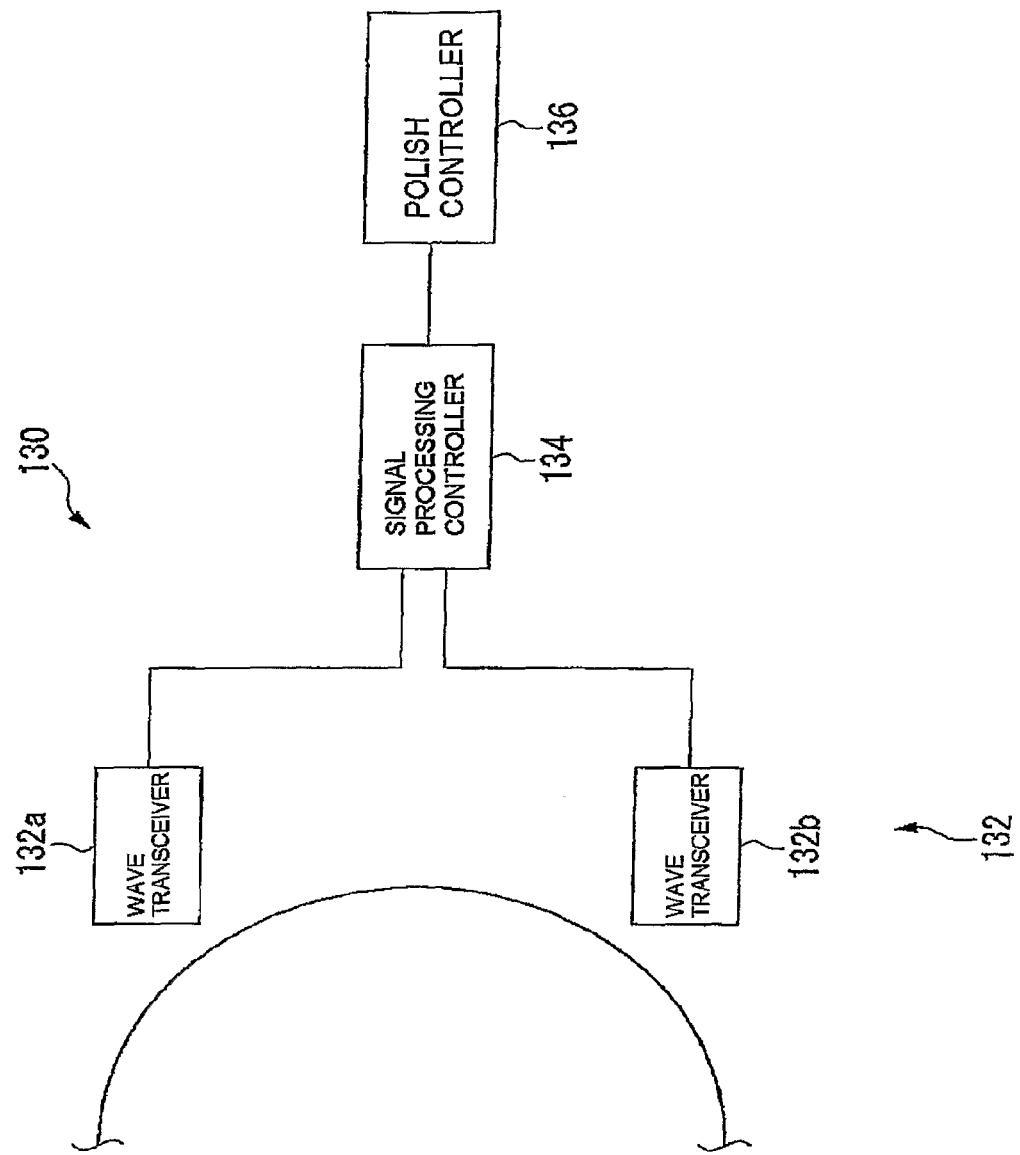
FIG. 15 is a diagram showing a configuration of the case, in which a plurality of kinds of transmission waves are utilized.

FIG. 15 shows a substrate peripheral portion polishing apparatus of this embodiment schematically. In the substrate peripheral portion polishing apparatus 130, a wave transceiver unit 132 is composed of a first wave transceiver 132a and a second wave transceiver 132b. The first wave transceiver 132a performs the projection/reception of the first transmission wave, and the second wave transceiver 132b performs the transmission/reception of the second transmission wave. The first transmission wave and the second transmission wave are exemplified by a laser light, a white light, a microwave, an ultrasonic wave or an alternating magnetic field signal. The first transmission wave and the second transmission wave are of different kinds. In case the transmission wave is the laser light, the wave transceiver unit is the aforementioned projecting/receiving unit.

A signal processing controller 134 receives the electric signal of the first reflected wave corresponding to the first transmission wave, from the first wave transceiver 132a, and processes the signal of the first reflected wave to determine the state of the wafer peripheral portion. Moreover, the signal processing controller 134 receives the electric signal of the second reflected wave corresponding to the second transmission wave, from the second wave transceiver 132b, and processes the signal of the second reflected wave to determine the state of the wafer peripheral portion.

The signal processing controller 134 controls the first wave transceiver 132a and the second wave transceiver 132b to cause either of them to perform the wave transmission/reception. Moreover, the signal processing controller 134 processes the signal obtained from one of the first wave transceiver 132a and the second wave transceiver 132b, to detect the state of the peripheral portion. As a result, the first transmission wave and the second transmission wave are selectively utilized.

The signal processing controller 134 may also cause both the first wave transceiver 132a and the second wave transceiver 132b to perform the wave transmission/reception. Moreover, the signal processing controller 134 may also determine the state of the wafer peripheral portion from the signal which is obtained from one of the first wave transceiver 132a and the second wave transceiver 132b. In this case, too, the first transmission wave and the second transmission wave are selectively utilized.

Here is described the mode of switching the transmission wave to be used for the measurement. Here are described three preferred patterns.

(1) In the first pattern, the signal processing controller 134 changes the kind of the transmission wave in accordance with the material of the peripheral portion of the wafer to be measured. As a result, the transmission wave suited for the material of the peripheral portion can be used to improve the measurement sensitivity and the measuring ability.

(2) In the second pattern, the signal processing controller 134 changes the kind of the transmission wave to be used in the measurement, in accordance with the proceeding situation of the polishing procedure. The proceeding situation of the polishing procedure is obtained from the signal of the reflected wave. In this embodiment, one transmission wave is used in the first half of the polish, and the other transmission wave is used in the second half of the polish.

When the polish is started, more specifically, one transmission wave is used to monitor the state of the wafer peripheral portion. When the wafer peripheral portion comes into a predetermined state, the transmission wave to be used for the measurement is interchanged. Then, the state of the wafer peripheral portion is monitored with the other transmission wave, and the polish end point is detected.

By thus changing the kind of the transmission wave in accordance with the progress of the polish, the proper transmission wave can be used to improve the measurement sensitivity and the measuring ability.

(3) In the third pattern, the signal processing controller 134 changes the kind of the transmission wave in accordance with the polishing condition. The information on the polishing condition is fed from the polish controller 136 to the signal processing controller 134. For example, it is assumed that the high-speed mode and the low-speed mode are set as the polishing condition. The high-speed mode is set in the first half of the polish, and the low-speed mode is set in the second half of the polish.

In this case, the signal processing controller 134 changes the kind of the transmission wave when the polishing condition changes. In a multi-step polish for which a plurality of polishing conditions are set, therefore, the transmission wave to be used for the measurement is interchanged in association with the polishing condition.

In this embodiment, by thus changing the kind of the transmission wave in accordance with the polishing condition, a proper transmission wave can be used to improve the measurement sensitivity and the measuring ability.

In the foregoing description, the transmission waves of two kinds are used. On the contrary, it is natural that transmission waves of three kinds or more can be used. It is also natural that a plurality of wave transceivers can be disposed for the transmission waves of the individual kinds. In the foregoing description, the three patterns are explained. Of these three, two or more patterns may also be suitably combined.

[Joint Use of Peripheral Portion Measurement and Control Parameter of Polishing Tool]

Here is described a proper embodiment, in which the peripheral portion measurement and the control parameter of the polishing tool are jointly used. In the foregoing embodiment, as described with reference to FIG. 1, the polishing tool is the polishing tape 32, which is pushed to the wafer 14 by the actuator 36, and this actuator 36 is made of the cylinder. In this embodiment, on the contrary, the actuator 36 is provided with a control motor. In this case, the torque current of the control motor can be used as the control parameter of the polishing tool. In this embodiment, moreover, the polish is controlled by using the torque current and the peripheral portion measurement result.

In this embodiment, more specifically, when the polish is started, the polish controller 40 monitors the torque current. When the torque current reaches a predetermined threshold value, the polish controller 40 instructs the signal processing controller 54 of the start of measurement. In accordance with this instruction, the signal processing controller 54 starts the measurement with the signal obtained from the projecting/receiving unit 52. Moreover, the signal processing controller 54 informs the polish controller 40 of the detection of the polish end point when it detects the polish end point. The polish controller 40 controls the motor and so on to end the polish.

Thus, in this embodiment, the substrate polish is controlled on the basis of the polishing state and the control parameter of the polishing tool, so that the polish can be properly controlled by using the control parameter.

In this embodiment, on the other hand, the control based on the control parameter and the control based on the polishing state are interchanged according to the progress of the substrate polishing procedure. In the aforementioned example, a coarse control is made in the first half of the polish on the basis of the control parameter, and a fine control is made in the second half of the polish by using the reflected wave. Thus, the polish control can be made by using the control parameter properly.

In this embodiment, too, transmission waves of a plurality of kinds may be selectively used as in the foregoing embodiment. These transmission waves may also be used together with the control parameter of the polishing tool.

[Zone Treatment]

Here is described a preferred embodiment for the zone treatment. This zone treatment is realized by a signal processing controller.

Figure 16:
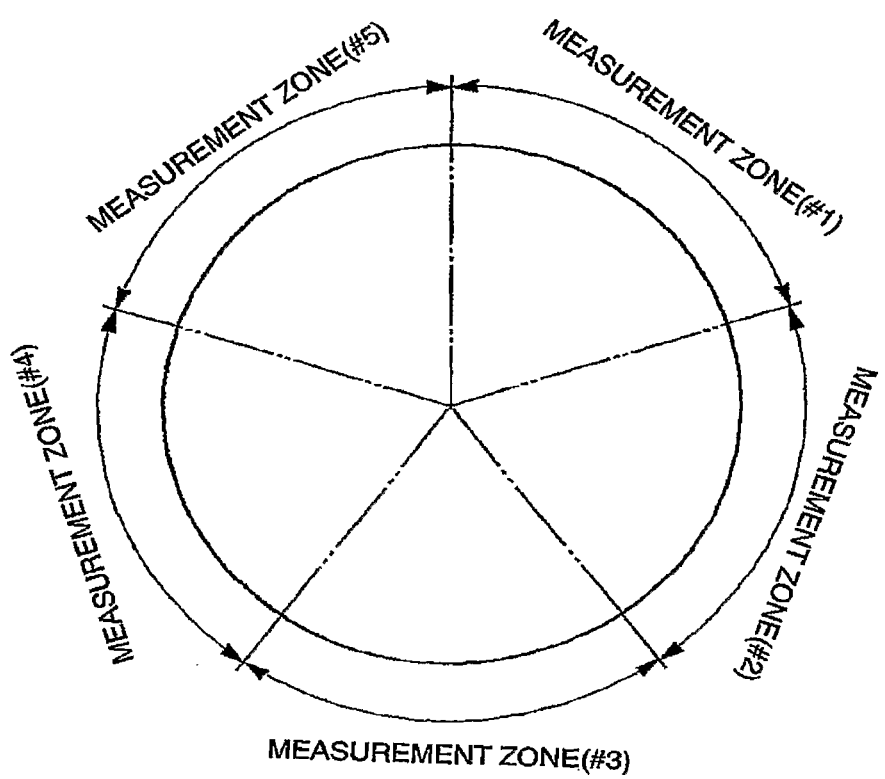
FIG. 16 is a diagram showing measurement zones for a zone treatment.

In the zone treatment, as referred to FIG. 16, a plurality of measurement zones are provided along the outer circumference of the wafer when the signal of the laser reflected light is to be processed. In the shown example, the wafer outer circumference is divided into five measurement zones. In the zone treatment, moreover, zone data are determined from the measurement zones. The zone data represent the signals of reflected lights obtained from the measurement zones. Moreover, these zone data are used to determine the state of the wafer peripheral portion.

In this embodiment, the wafer is turned, but the projecting/receiving unit is fixed. As the wafer is turned, therefore, the reflected light is obtained from the entire circumference of the wafer. The data of the entire zone are divided into the data of a plurality of zones.

The boundaries of the measurement zones may be either at arbitrary positions on the wafer outer circumference or at preset positions. In this latter case, the signal processing controller acquires information on the wafer turning angle thereby to determine the positions of the boundaries from the information on the wafer turning angle. The reference of the wafer turning angle is exemplified by the positions of notches.

The zone data represent the signals of reflected lights obtained from the measurement zones, as described hereinbefore. The zone data are exemplified by the average value, the maximum, the level difference (or range) and the like of the effective amplitudes of the reflected lights in the measurement zones. Moreover, the zone data may be expressed by the time differentiations of the effective amplitudes of the reflected lights in the measurement zones, and the time differentiations may be of a first degree, a second degree or more degrees.

The zone data of all measurement zones may be used for processing them. There may also be used the zone data of one or more predetermined measurement zones. There may also be used the zone data of one or more arbitrarily selected measurement zones.

The zone data are compared with a preset designated value so that the polish end point is detected. When the zone data come into a predetermined designated range, for example, the polish end point is detected. The polish end point is also detected, when the zone data become a predetermined designated value or higher. Alternatively, the polish end point may also be detected when the zone data become a predetermined designated value or lower.

In the zone data processing, the following zone converging operation may also be preferably carried out. In the zone converging operation, the zone data of a plurality of measurement zones are compared.

In the zone converging operation, one measurement zone is designated. It is then decided whether or not the difference in the zone data between the designated zone and the remaining zones is at a predetermined threshold value or smaller. The polish end point is detected when the difference in the zone data is at the threshold value or smaller. In the zone converging operation, the zone data may represent the effective amplitudes of the measurement zones or may be the time differentiation.

In this embodiment thus far described, the state of the substrate peripheral portion can be properly grasped by using the zone data thereby to improve the measuring ability.

By comparing the zone data of the measurement zones, moreover, the situation of the peripheral portion can be grasped with reference to the measurement zones so that the detection sensitivity of the state of the peripheral portion is improved. As a result, the state of the substrate peripheral portion can be properly grasped to improve the measuring ability.

[Target Setting Operation]

In addition, the substrate peripheral portion measuring device of this embodiment may also set the target of the polish end point thereby to perform the measurements with the set target, as described in the following.

In this operation, the signal processing controller determines the remaining amount of polish from the signal of the reflected light obtained at the initial stage of the polish, and sets the target of the polish end point. This polish end point target indicates the reflected light, which is obtained when the polish of the remaining amount is ended so that the wafer peripheral portion becomes smooth. The remaining amount of polish and the target of the polish end point are expressed by the effective amplitude of the reflected light, for example.

The signal processing controller holds and uses the target of the polish end point to detect the polish end point. Here, the signal of the reflected wave inputted is compared with the target of the polish end point. This polish end point is detected when the input signal reaches the target of the polish end point. The polish controller is informed of the polish end point to end the polish.

Thus, this embodiment can detect the polish end point properly by setting the target of the polish end point.

[End Time Setting Operation]

On the other hand, the substrate peripheral portion measuring device of this embodiment may also be configured to set the polish end time, as described in the following.

In this operation, there is determined at first the reference time $t1$ till the predetermined reference polished state is obtained in the polishing procedure. An auxiliary time ta is calculated from the reference time $t1$ and a predetermined coefficient $k1$. For example, $ta=t1 \times k1$. The auxiliary time ta is calculated by $ta=t1 \times k1$, $ta=t1/k1$, $ta=t1+k1$, $ta=t1-k1$ and so on. The auxiliary time ta is a time period from the reference time $t1$ to the polish end point. Therefore, a polish end time $t2$ (i.e., the time period from the polish START TIME to the polish end time) is expressed by $t1+ta$. The additional polish is carried from the reference time $t1$ to the polish end time $t2$.

The polish end time $t2$ is sent from the signal processing controller to the polish controller so that it is applied for controlling the polish in the polish controller. In this embodiment, the polish end time $t2$ is properly set by using a sample wafer. The polish end time $t2$ is held in the polish controller and is applied, after the sample wafer is processed, for treating a plurality of wafers.

Thus, in this embodiment, the polishing time can be precisely set by using the information on the polishing state obtained by the measurements during the polish. Moreover, the polishing time can be simply set.

The target setting operation and the end time setting operation have thus far been described. Either the polishing ending target or the polish end time may also be set depending on the material of the wafer to be treated. Alternatively, operation may be carried out by using both of them, and either setting time (i.e., an earlier time or a later time) may also be set as the end time, if necessary.

[Use of Relation between Peripheral Portion Material and Reflection]

On the other hand, the substrate peripheral portion measuring device of this embodiment may also decide the state of the wafer peripheral portion on the basis of the change in the reflection according to the material change of the surface of the peripheral portion of the wafer accompanying the treatment of the wafer, as described in the following example.

Here, it is assumed that the silicon nitride (SiN) film of the peripheral portion of a silicon (Si) wafer is removed. Silicon and silicon nitride are different in the absorption wavelength characteristics as optical characteristics. The silicon nitride film absorbs a wavelength of 320 nm or less. On the contrary, the silicon wafer reflects the whole wavelength.

It is, therefore, set that the wavelength of the laser light is absorbed by the silicon nitride film. The wavelength of the laser light is set to 240 to 320 nm, for example.

At the initial stage of the polish, the silicon nitride film exists on the wafer surface so that the optical reflection is low. As the polish of the peripheral portion proceeds, the material of the wafer surfaces changes from the silicon nitride into the silicon. When this silicon appears, the quantity of the reflected light abruptly rises. This optical change is detected by the signal processing controller. The polish end point is detected when a predetermined optical change appears. This optical change is so prominent that the end point is precisely detected.

Thus, noting the change in the reflection according to the change in the material of the surface of the peripheral portion, the state of the peripheral portion can be precisely decided to improve the measuring ability.

[Use of Relation between Peripheral Portion Material and Reflection Pattern]

On the other hand, the substrate peripheral portion measuring device of this embodiment may also decide the state of the peripheral portion on the basis of the change in the reflected pattern according to the material change of the surface of the peripheral portion accompanying the treatment of the wafer, as described in the following example.

When the output of the laser light is properly adjusted, a pattern appears in the reflected light. In this embodiment, this reflected pattern is used.

Here, it is assumed that the silicon nitride film (SiN) is removed from the peripheral portion of the silicon wafer (Si). As the polish proceeds, the silicon nitride film is removed to expose the silicon wafer to the outside.

Figure 17:
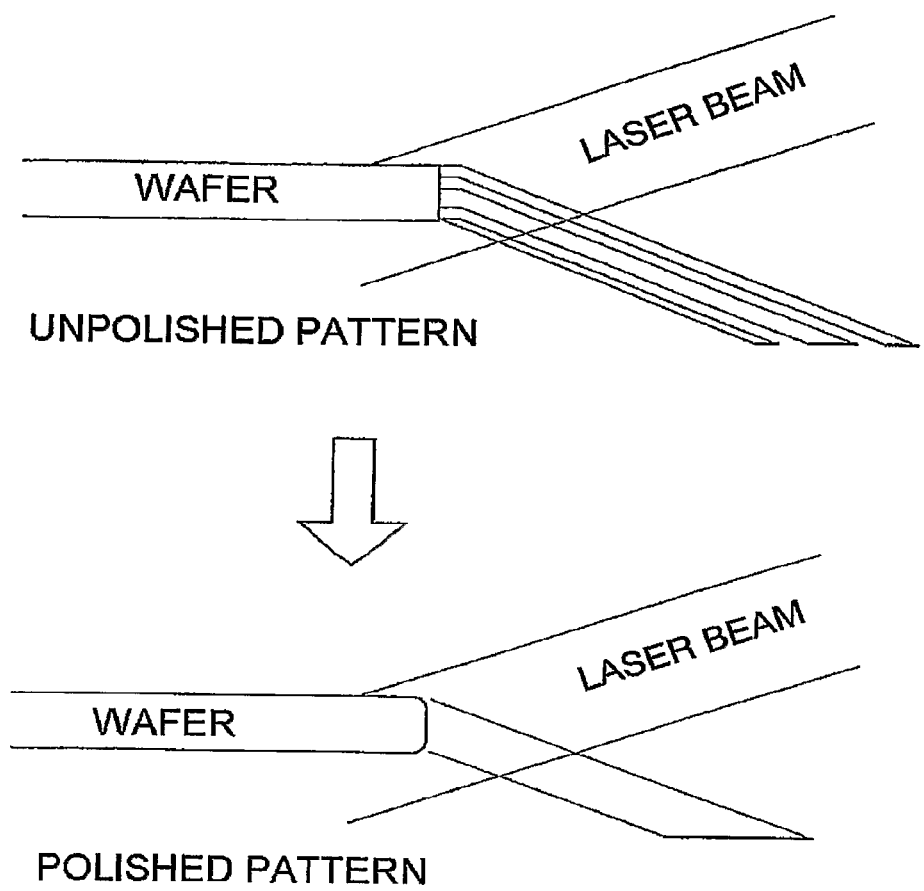
FIG. 17 is a diagram showing a change in the pattern of a reflected light.

With the irradiation of a collimated laser beam of a specific wavelength, as shown in FIG. 17, a significant difference appears in the reflected pattern between the silicon nitride film (unpolished) and the silicon (polished). On the silicon nitride film, a fringe pattern appears in the reflected pattern due to the diffraction of the film edge. On the contrary, no fringe pattern appears in the reflected pattern from the polished face of the silicon. This change in the pattern is detected.

For the pattern detection, the signal of the reflected pattern is subjected to an IV conversion (i.e., a current-voltage conversion) by a photodiode in the projecting/receiving unit. Alternatively, this projecting/receiving unit may be provided with a high-speed image taking device. This image taking device (or an image pickup device) is provided with a CCD or CMOS camera, for example. The pattern thus obtained is subjected to a pattern recognition treatment. In the example described, the polish end point is detected when the fringe pattern in the pattern disappears.

Thus in this embodiment, by noting the change in the reflected pattern in accordance with the material change of the surface of the peripheral portion, the state of the peripheral portion can be precisely decided to improve the measuring ability.

Thus, it is possible to use the change in the reflection and the change in the reflected pattern. The reflection or the reflected pattern may be separately used according to the state of the wafer peripheral portion of the object to be measured.

[Substrate Treating Apparatus with Substrate Peripheral Portion Polishing Apparatus]

Figure 18:
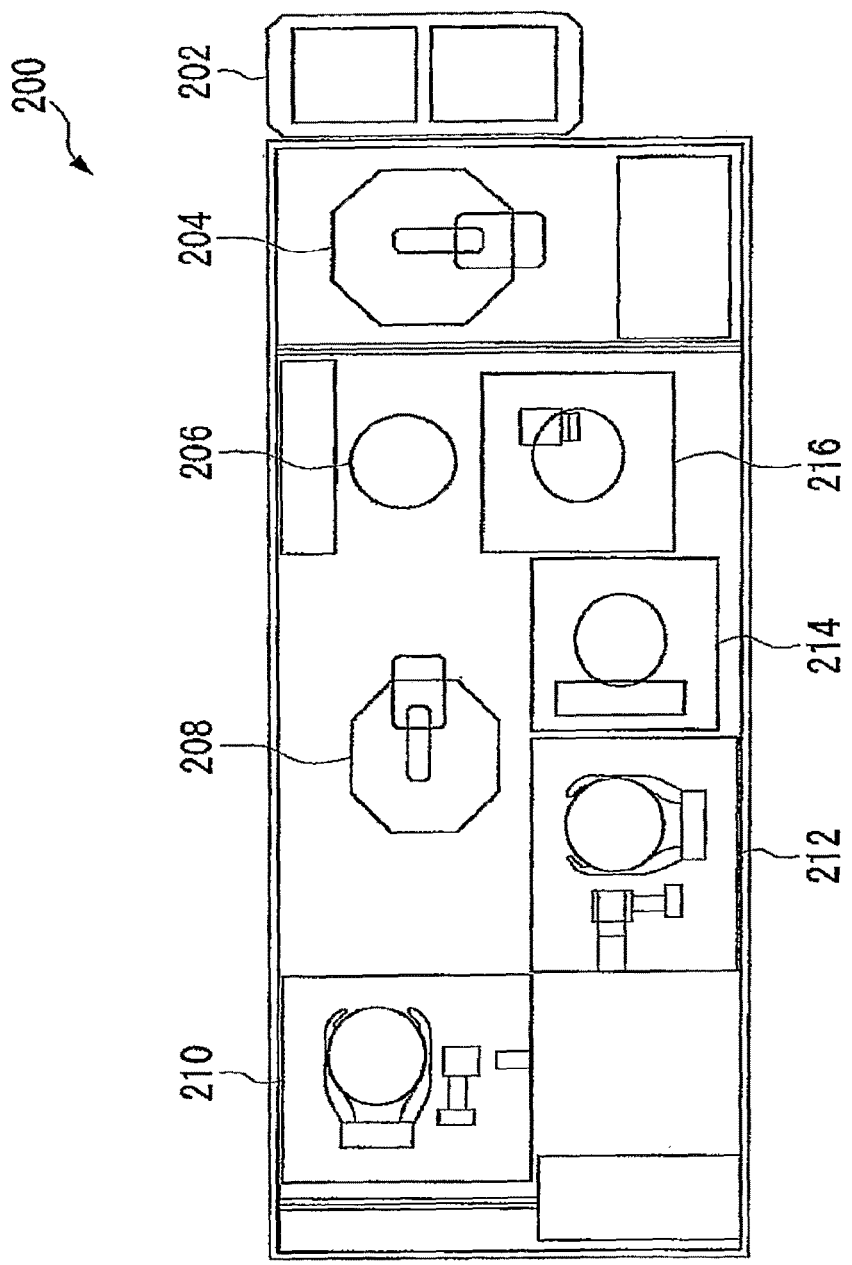
FIG. 18 is a diagram showing a substrate treating apparatus which is provided with the substrate peripheral portion polishing apparatus.

Next, FIG. 18 shows an example of the substrate treating apparatus which is provided with the substrate peripheral portion polishing apparatus of this embodiment. The substrate treating apparatus 200 is provided with a load/unload unit 202, a first transfer robot 204, a substrate stage 206 (or a buffer), a second transfer robot 208, a notch polishing module 210, a bevel polishing module 212, a primary rinsing module 214 and a secondary rinsing module 216.

The wafer is transferred by the first transfer robot 204 from the load/unload unit 202 to the substrate stage 206. Then, the wafer is sequentially transferred by the second transfer robot 208 to the notch polishing module 210, the bevel polishing module 212, the primary rinsing module 214 and the secondary rinsing module 216. The first transfer robot 204 returns the rinsed wafer to the load/unload unit 202.

In FIG. 18, the bevel polishing module 212 corresponds to the substrate peripheral portion polishing apparatus thus far described. The substrate peripheral portion measuring device of this embodiment also belongs to the bevel polishing module 212.

In an applied example of this embodiment, moreover, the wafer evaluating face is set on the end face or back face of the wafer. The evaluation is timed during or after the polish. For this evaluation, the polished state during the polish is monitored, the polish end point during the polish is detected, or the presence/absence of a defect in the polished wafer is decided. In the monitor of the polished state of the defected portion, for example, the end face polish is interrupted at a stage midway of the end face polish, and the wafer is saved. The remaining defect (or the residual of the defect polish) is measured. The necessary time for the additional polish is calculated from the measurement result so that the additional polish is performed. The wafer is moved again from the polish position to the saving position (as indicated at 206 in FIG. 18) for the measurement so that the remaining polish is measured. Thus, a series of operations are carried out by an initial polish, a measurement at the saving position, an additional polish, a re-save, a re-measurement and an additional polish. The measurement and the additional polish may be repeated. The peripheral portion is polished by those series operations. The polish time can also be determined.

[Application to Rinsing Apparatus (for Rinsing after Plating)]

Here is described an embodiment for incorporating the substrate peripheral portion measuring device into the rinsing apparatus. In the description thus far made, the substrate peripheral portion measuring device is incorporated into the substrate peripheral portion polishing apparatus. In the following description, on the other hand, the substrate peripheral portion measuring device is incorporated into the rinsing apparatus. This rinsing apparatus is exemplified by a rinsing apparatus related to a plating operation, a rinsing apparatus related a CMP (Chemical-Mechanical Polish), and a rinsing apparatus related to an etching operation. The defect and unnecessary substance of the peripheral portion can be detected by measuring the peripheral portion with the rinsing apparatus.

Figure 19:
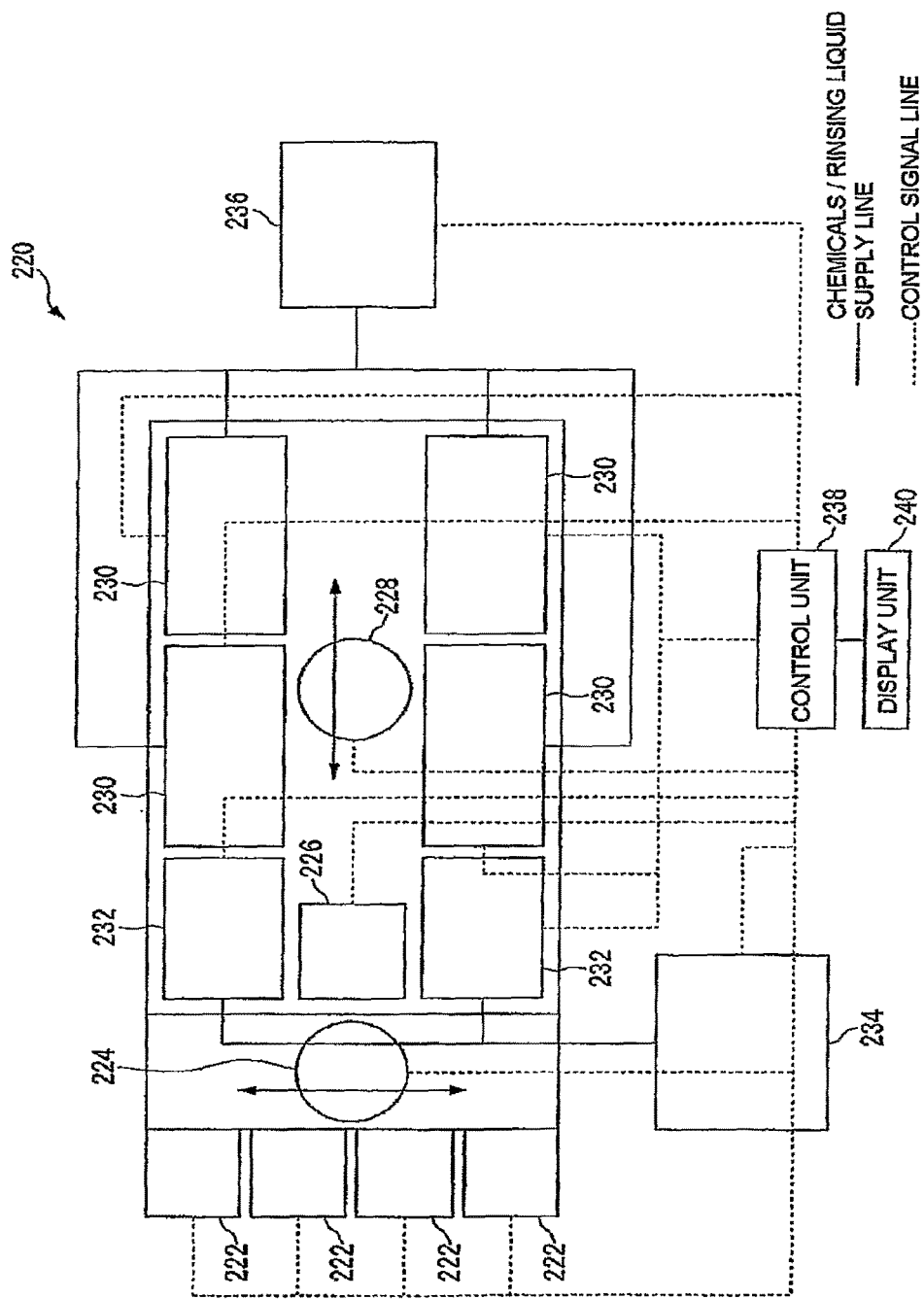
FIG. 19 is a diagram showing a plating substrate treating apparatus, which is provided with a rinsing apparatus.

FIG. 19 shows a plating substrate treating apparatus. This substrate treating apparatus 220 is provided with a substrate cassette 222, a first transfer robot 224, a substrate stage 226 (or a temporary stage), a second transfer robot 228, a plating bath 230, a rinsing apparatus 232, a rinsing liquid and chemicals supply device 234, a plating chemicals supply device 236, a control unit 238 and a display unit 240.

The substrate is transferred by the first transfer robot 224 from the substrate cassette 222 to the substrate stage 226. The substrate is further transferred by the second transfer robot 228 to the plating bath 230 and the rinsing apparatus 232. The plating bath 230 is supplied with the plating chemicals from the plating chemicals supply device 236. On the other hand, the rinsing apparatus 232 is supplied with the chemicals and the rinsing liquid from the rinsing liquid and chemicals supply device 234. The rinsing treatment and the drying treatment are carried out in the rinsing apparatus 232. The substrate rinsed is returned to the substrate cassette 222.

In the configuration of FIG. 19, the rinsing apparatus 232 is preferably provided with the substrate peripheral portion measuring device. In the rinsing apparatus 232, the turning wafer is fed with the rinsing liquid as in the ordinary rinsing apparatus. In this state, the substrate peripheral portion measuring device is provided for measuring the wafer peripheral portion.

Figure 20:
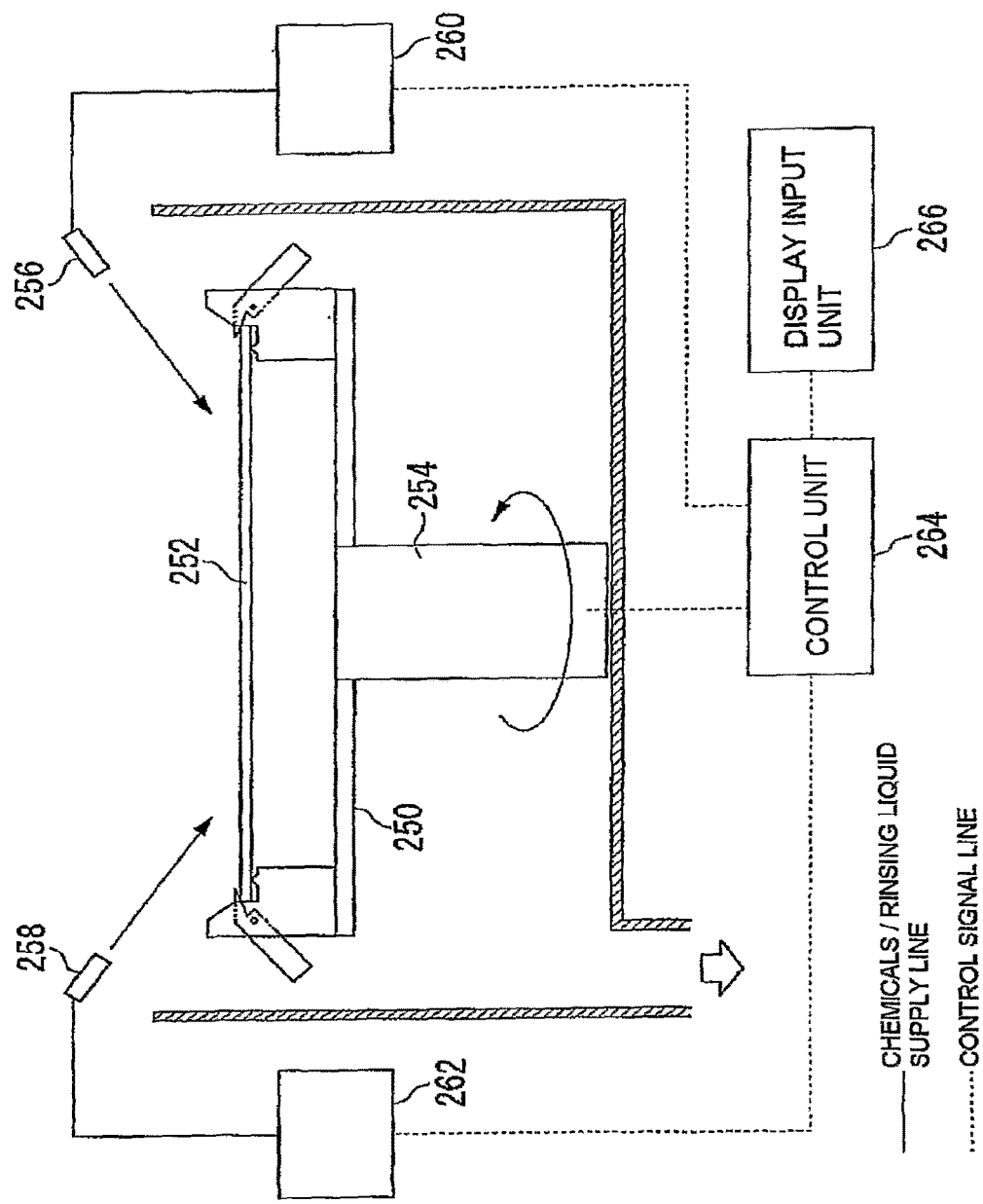
FIG. 20 is a diagram showing the rinsing apparatus.

FIG. 20 shows an example of the configuration of the rinsing apparatus 232. In this rinsing apparatus 232, a base unit 250 holds a wafer 252. On the other hand, the base unit 250 is supported by a shaft 254 so that it turns together with the wafer 252.

The base unit 250 is provided with a wafer holding member. As shown, this wafer holding member is turnably supported by a turning pin. This turning pin pivots the portion of the wafer holding member above the center of gravity. The wafer holding member is so arranged as is made parallel to the shaft 254 by its own weight when the wafer stands still. As the shaft 254 turns, a centrifugal force occurs in the wafer holding member. By this centrifugal force, the lower portion (i.e., the portion of the wafer holding member below the turning pin) is moved outward and is raised. As a result, the upper portion (i.e., the portion of the wafer holding member above the turning pin) falls down inward to hold and grip the wafer. At least three wafer holding portions are disposed in the circumferential direction.

The wafer 252 is fed on its surface with a rinsing liquid from a rinsing liquid feeding nozzle 256 and with chemicals from a chemicals feeding nozzle 258. The rinsing liquid feeding nozzle 256 is supplied with the rinsing liquid from a rinsing line supply line 260, and the chemicals feeding nozzle 258 is supplied with the chemicals from a chemicals supply line 262. Moreover, the wafer turns and liquid supply are controlled by a control unit 264, which is connected with a display input unit 266.

Typically in the rinsing apparatus of FIG. 20, the rinsing liquid is water (or pure water) or gas-dissolved water. The rinsing apparatus is properly provided with a peripheral portion measuring device for measuring the peripheral portion while being fed with the rinsing liquid. The peripheral portion measuring device may measure the peripheral portion when the chemicals are fed.

[Application to Rinsing Apparatus (Rinsing after CMP)]

Figure 21:
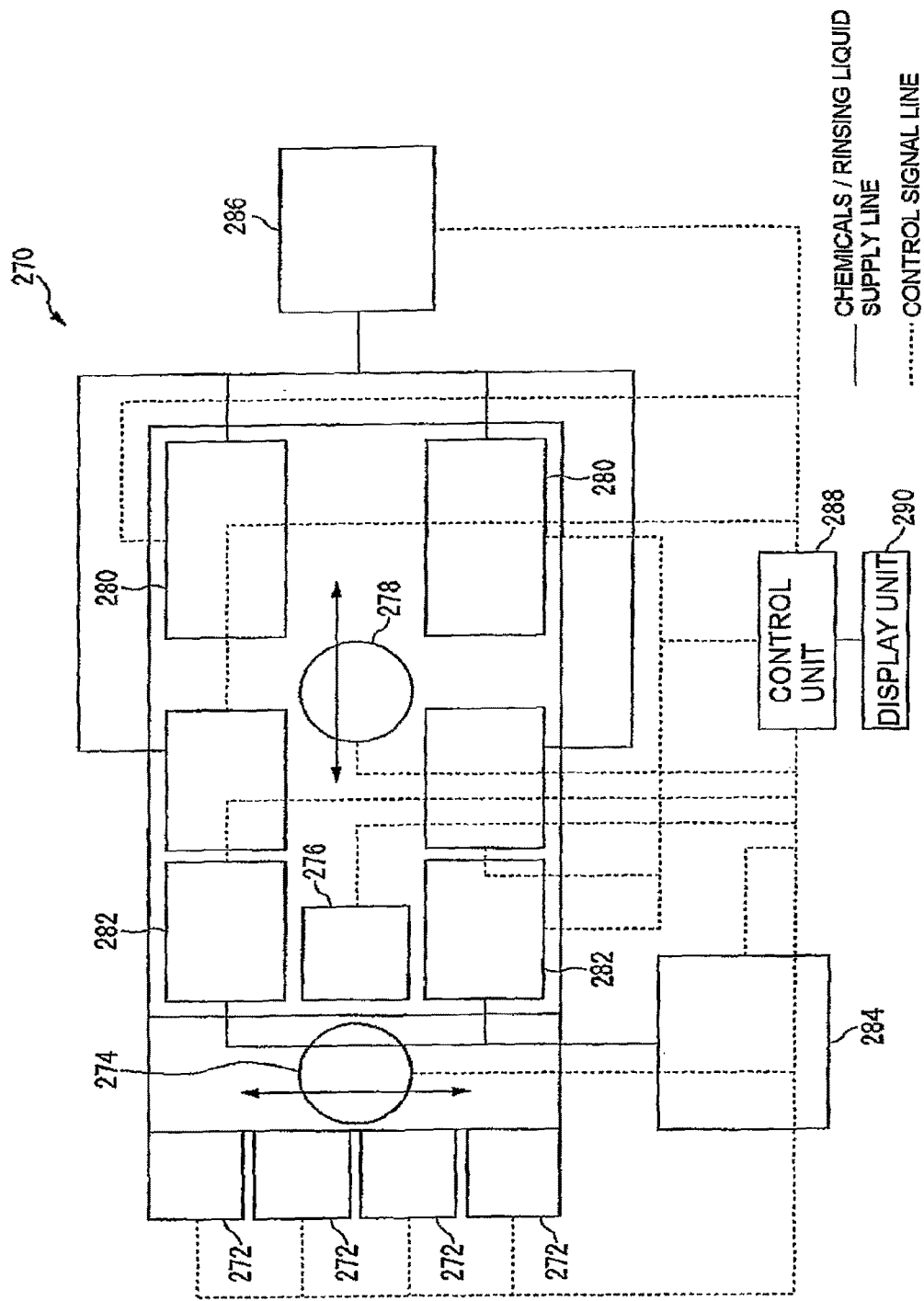
FIG. 21 is a diagram showing a CMP substrate treating apparatus, which is provided with the rinsing apparatus.

FIG. 21 shows a CMP substrate treating apparatus. This substrate treating apparatus 270 is provided with a substrate cassette 272, a first transfer robot 274, a substrate stage 276 (or a temporary stage), a second transfer robot 278, a polishing module 280, a rinsing apparatus 282, a rinsing liquid and chemicals supply device 284, a slurry supply device 286, a control unit 288 and a display unit 290.

The substrate is transferred by the first transfer robot 274 from the substrate cassette 272 to the substrate stage 276. The substrate is further transferred by the second transfer robot 278 sequentially to the polishing module 280 and the rinsing apparatus 282. The polishing module 280 is supplied with the slurry from the slurry supply device 286. On the other hand, the rinsing apparatus 282 is supplied with the chemicals and the rinsing liquid from the rinsing liquid and chemicals supply device 284. The rinsing apparatus 282 performs the rinsing operation with the chemicals and the drying operation. The substrate rinsed is returned to the substrate cassette 272.

In the configuration of FIG. 21, the rinsing apparatus 282 is properly provided with the substrate peripheral portion measuring device. In the rinsing apparatus 282, as in the ordinary rinsing apparatus, the turning wafer is fed thereon with the rinsing liquid. The substrate peripheral portion measuring device is provided for measuring the wafer peripheral portion in that state. The configuration of rinsing apparatus may be one shown in FIG. 20.

[Application to Rinsing Apparatus (Rinsing after Etching)]

Figure 22:
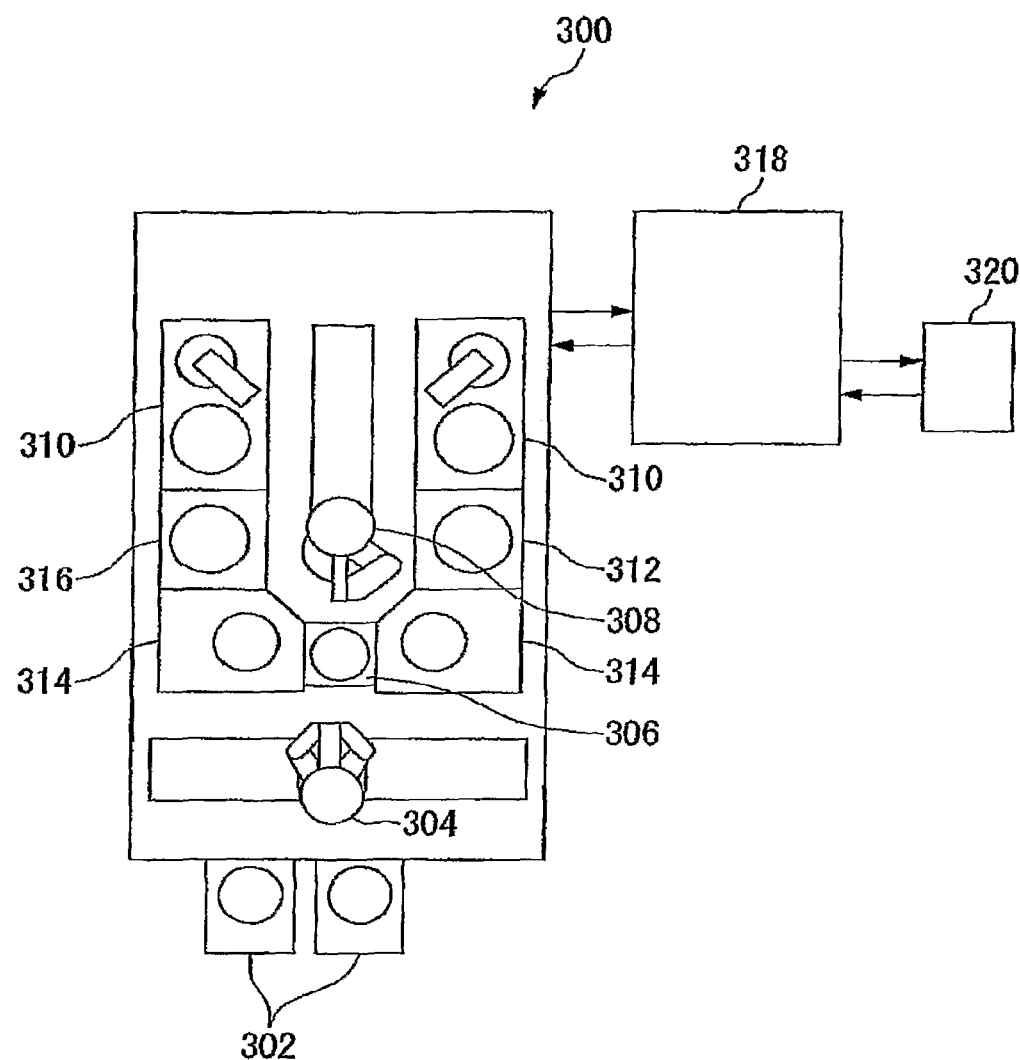
FIG. 22 is a diagram showing plating substrate treating apparatus, which is provided with the rinsing apparatus.

FIG. 22 shows a plating substrate treating apparatus. This substrate treating apparatus 300 is used for forming fine copper wiring over the substrate. The substrate treating apparatus 300 is provided with a substrate load/unload unit 302, a first transfer robot 304, a substrate stage 306, a second transfer robot 308, a plating device 310, a bevel etching device 312, a rinsing apparatus 314, a heat treating (annealing) device 316, a plating liquid tank 318 and a plating liquid analyzing device 320.

The substrate is transferred by the first transfer robot 304 from the substrate cassette of the substrate load/unload unit 302 to the substrate stage 306. The substrate is further transferred by the second transfer robot 308 sequentially to the plating device 310 and the bevel etching device 312.

The bevel etching device 312 subjects the substrate peripheral portion to an etching treatment. In the bevel etching device 312, for example, the substrate is continuously fed, while being held horizontally and turned, at the central portion on its surface side with an acid solution. The substrate is continuously or intermittently fed at its circumferential peripheral portion with an oxidizer solution.

The acid solution may be a non-oxidizing acid such as hydrofluoric acid, hydrochloric acid, sulfuric acid, citric acid or oxalic acid. The oxidizer solution used is any of ozone water, an aqueous solution of hydrogen peroxide, an aqueous solution of nitric acid and an aqueous solution of hypochlorous acid. These may be used in combination. Copper or the like is filmed on or stuck to the circumferential peripheral portion of the substrate. Such copper or the like is abruptly oxidized in the oxidizer solution, and is etched and dissolved with the oxide solution fed from the central portion of the substrate so that it is removed. The oxide solution spreads from the substrate center over the entire surface.

After bevel-etched, the substrate is transferred by the second transfer robot 308 to the rinsing apparatus 314. In this rinsing apparatus 314, the surface of the substrate is rinsed with the chemicals or the rinsing water such as pure water, and is subjected to a spin drying treatment.

Then, the substrate is further transferred to the heat treating device 316. After the heat treatment in the heat treating device 316, the substrate is transferred by the second transfer robot 308 to the substrate stage 306. Moreover, the substrate is returned by the first transfer robot 304 to the substrate load/unload unit 302.

In the configuration of FIG. 22, the rinsing apparatus 314 is properly provided with the substrate peripheral portion measuring device. In the rinsing apparatus 314, the turning wafer is fed with the rinsing liquid. The substrate peripheral portion measuring device is provided for measuring the wafer peripheral portion in this state. By this peripheral portion measurement, it is inspected whether or not the portion is left unetched.

In case the unetched portion is detected by the peripheral portion measurement, on the other hand, the wafer may be transferred to the bevel etching device 312 and returned to the etching step. At another step, on the other hand, the unetched portion may be removed. The re-treatment or the like according to the measurement result at such rinsing step may also be carried out in the aforementioned other embodiments.

[Other Modes]

In the peripheral portion polishing substrate treating apparatus 200, as shown in FIG. 18, the bevel polishing module 212 acting as the substrate peripheral portion polishing apparatus is provided with the substrate peripheral portion measuring device. On the contrary, the substrate peripheral portion measuring device may also be disposed in the notch polishing module 210. On the other hand, the substrate peripheral portion measuring device may also be disposed in the primary rinsing module 214 or the secondary rinsing module 216 acting as the rinsing apparatus. In this modification, the polish is once ended, and the peripheral portion is measured at the rinsing step. If a re-polish is necessary, the wafer is returned to the polishing step.

In the bevel etching substrate treating apparatus 300, as shown in FIG. 22, the rinsing apparatus 314 is provided with the substrate peripheral portion measuring device. On the contrary, the substrate peripheral portion measuring device may also belong to the bevel etching device 312. In this case, the peripheral portion is measured during the etching operation. The peripheral portion is measured while the wafer is being fed with the etching chemicals in place of the water.

Moreover, the peripheral portion may also be measured after having been cleared of the chemicals, as has been described in the foregoing embodiment.

As exemplified in those examples, the peripheral portion measuring device may also be disposed in the etching or polishing removing apparatus so that it may measure the peripheral portion during the removing operation thereby to detect the end point or the like. Moreover, the peripheral portion measuring device may also be disposed in the rinsing apparatus which is provided together with the aforementioned removing apparatus so that it may perform the measurement while the removing treatment being interrupted.

In addition, the substrate peripheral portion measuring device may also be disposed in another apparatus. Moreover, the substrate peripheral portion measuring device may be solely disposed. In this modification, the substrate is held and turned for the measurement, and the wafer is fed with a liquid (e.g., water) for the measurement.

The invention has been described in connection with its preferred embodiments. However, the invention should not be limited to the aforementioned embodiments but could naturally be modified within the scope of the invention by those skilled in the art.

[Examples]

Figure 23:
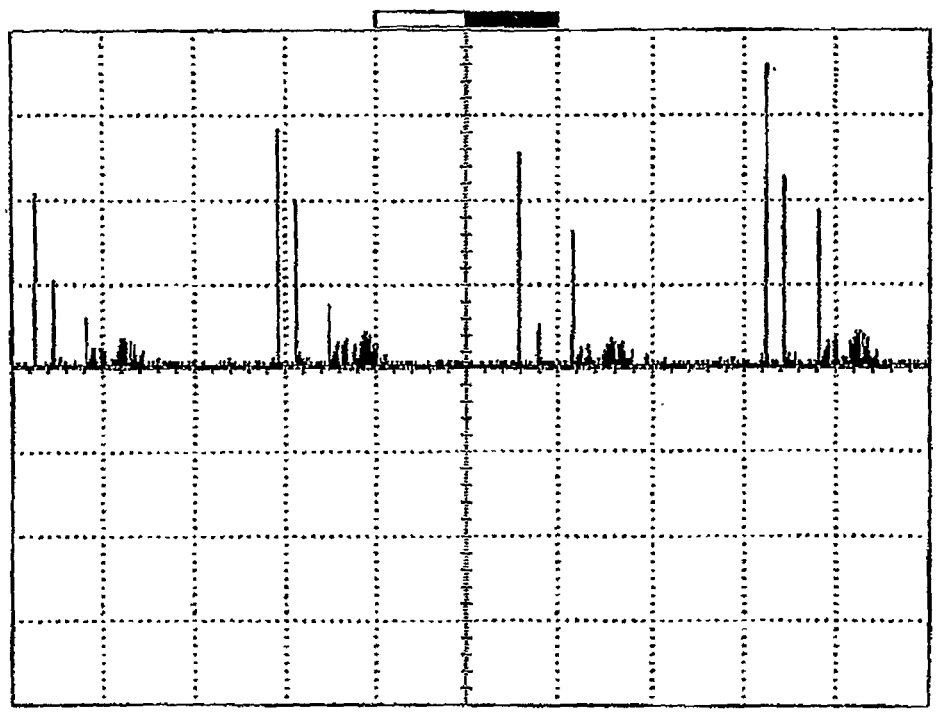
FIG. 23 is a diagram showing the measured data of an unpolished product.
Figure 24:
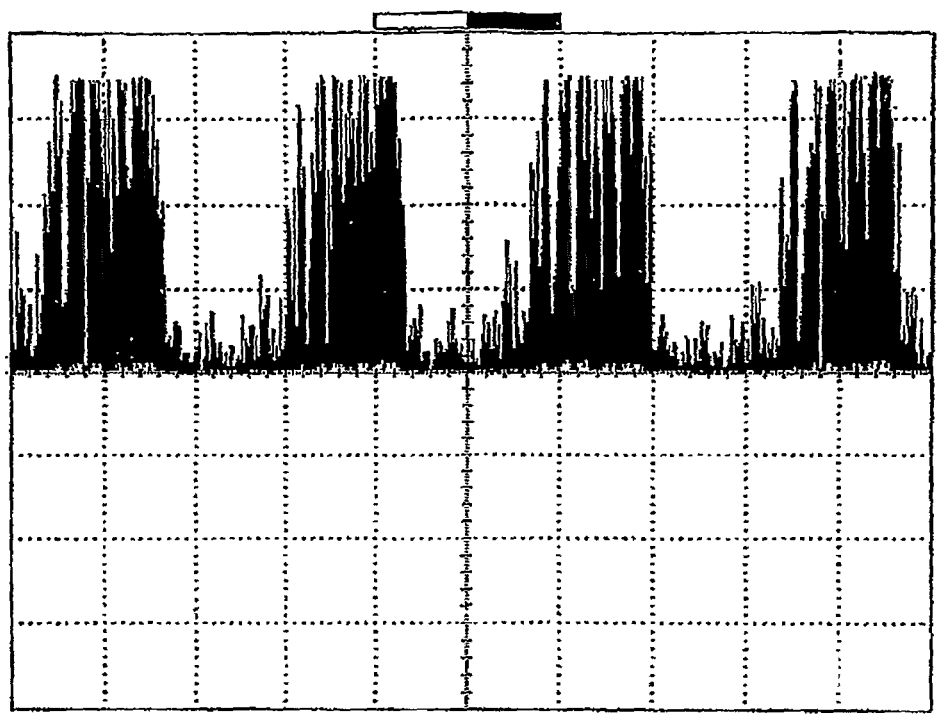
FIG. 24 is a diagram showing the measured data of a polished product.

FIG. 23 and FIG. 24 show the experimental data obtained by using the measuring device of the invention. The experimental data of FIG. 23 and FIG. 24 are the results of measurements using the laser beam, as shown in the embodiment of FIG. 3. FIG. 23 shows the measurement data of an unpolished product, and FIG. 24 shows the measurement data of a polished product.

In FIG. 23 and FIG. 24, the ordinate indicates the voltage at the time when the reflected light is expressed in terms of a DC voltage. One scale corresponds to 2 volts. The abscissa indicates the position in the circumferential direction of the wafer. The drawings show the data at the time when the wafer starts from the notch portion and returns after four turns to the notch portion. In other words, the whole range in the abscissa direction corresponds to the four circumferences of the wafer. 2.5 scales in the abscissa direction corresponds to one circumference of the wafer.

FIG. 23 shows the measurement data of the unpolished product, as described above. In the measurements, a pulsating laser light is projected from the optical fiber, and the reflected light is received by the optical fiber.

In FIG. 23, the quantity of the reflected light is small over a wide range. This indicates that the peripheral portion of the wafer is covered with the film of silicon nitride (SiN).

In FIG. 23, moreover, high spike signals are found. In some portions, the intensities of the reflected light are locally high. These portions indicate that the wafer is locally polished. At these portions, the wafer peripheral portion is polished for experiments so that the silicon nitride is damaged to expose the silicon (Si) locally to the outside. The exposure of silicon raises the intensities of the reflected signal.

FIG. 24 shows the measurement data of the polished article. In FIG. 24, the quantity of reflected light is large over a wide range. This indicates that the film of the silicon nitride of the wafer peripheral portion is polished away to expose the silicon (Si) to the outside. Observing the damaged portions in FIG. 23, the silicon nitride around the damage is removed so that the damage disappears.

By comparing the reflected lights before and after the polish, as shown in FIG. 23 and FIG. 24, it is possible to detect the polish end point (i.e., the end of the polish). For deciding the polish end point, as has already been described, it is arbitrary to use the change of a relative optical quantity, the change of an absolute value or the change of a differentiated value.

While there has been described what is at present considered to be preferred embodiments of the invention, it will be understood that various modifications may be made thereto, and it is intended that appended claims coverall such modifications as fall within the true spirit and scope of the invention.

INDUSTRIAL APPLICABILITY

The invention can measure the peripheral portion of a substrate and can be usefully employed in substrate manufacturing facilities.

The invention claimed is:

1. A substrate peripheral portion polishing apparatus comprising:
   a substrate holder for holding a substrate while the substrate rotates;
   a nozzle configured to supply a liquid to a center of rotation of the substrate such that the liquid flows along a surface of the substrate toward a peripheral portion of the substrate;
   a passage forming member configured to enclose the peripheral portion of the substrate and form a passage to feed the liquid onto the peripheral portion of the substrate;
   a polishing tape for polishing the peripheral portion of said substrate while the peripheral portion is supplied with the liquid;
   a wave transceiver configured to transmit a transmission wave to the peripheral portion of the substrate through a film of the liquid while the liquid is flowing on the peripheral portion through said passage forming member, and for receiving a reflected wave from the peripheral portion through the film of the liquid fed to the substrate;
   a signal processing controller is configured to processing the signal of the reflected wave to determine a polished state of the peripheral portion; and
   a polish controller is configured to controlling the polishing of the peripheral portion in accordance with the polished state of said peripheral portion obtained by said signal processing controller.

2. The substrate peripheral portion polishing apparatus of claim 1,
   wherein a wave transmitting/receiving portion of said wave transceiver is arranged within said passage formed by said passage forming member.

3. The substrate peripheral portion polishing apparatus of claim 2,
   wherein a wall face of said passage has a wave collecting face shaped to further reflect said reflected wave so as to collect the reflected wave; and
   wherein said wave transceiver has a receiving portion for receiving the reflected wave, said receiving portion being located at a position where the reflected wave is collected.

4. The substrate peripheral portion polishing apparatus of claim 1, further comprising:
   a water removing nozzle for blowing away the liquid from the peripheral portion;
   wherein said wave transceiver transmits the transmission wave to a location where the liquid is blown away by said water removing nozzle.

5. The substrate peripheral portion polishing apparatus of claim 1, further comprising:
a water blocking pad enveloping the peripheral portion and configured to block a portion of the liquid at the peripheral portion;
wherein said wave transceiver is configured to transmit/receive the wave through said water blocking pad.

6. The substrate peripheral portion polishing apparatus of claim 1,
wherein said signal processing controller is further configured to detect a polish end point of the peripheral portion; and
wherein said polish controller is further configured to end the polishing of the peripheral portion when said signal processing controller detects the polish end point of the peripheral portion.

7. The substrate peripheral portion polishing apparatus of claim 1,
wherein said signal processing controller is further configured to monitor a state of the polishing procedure of the peripheral portion; and
wherein said polish controller is further configured to control a polishing condition of the peripheral portion in accordance with the state of the polishing procedure of the peripheral portion.

8. The substrate peripheral portion polishing apparatus of claim 7,
wherein said polish controller is further configured to control at least one of a rotation speed of the substrate, a pushing force of a polishing tool to the peripheral portion, a feed movement of a polishing tape, a feed speed of the polishing tape, a relative movement of a polishing head with respect to the substrate, a relative moving speed of the polishing head with respect to the substrate, and a feed rate of the liquid.

9. The substrate peripheral portion polishing apparatus of claim 1,
wherein said signal processing controller is configured to determine whether or not the peripheral portion is defective.

10. The substrate peripheral portion polishing apparatus of claim 1, further comprising:
an abnormality detecting unit for determining whether a polish abnormality has occurred when a waveform of the reflected wave is abnormal;
wherein said polish controller is configured to stop a polishing procedure when the polish abnormality is detected by said abnormality detecting unit.

11. The substrate peripheral portion polishing apparatus of claim 1, further comprising:
a tool exchange informing unit for informing of an arrival of an exchanging timing of a polishing tool when a polishing rate obtained from the reflected wave lowers to a predetermined tool exchanging threshold rate.

12. The substrate peripheral portion polishing apparatus of claim 1
wherein said wave transceiver is configured to send a plurality of types of transmission waves; and
wherein a type of the transmission wave to be used for the measurement is changed according to a proceeding situation of a polishing procedure determined from the reflected wave.

13. The substrate peripheral portion polishing apparatus of claim 1,
wherein said wave transceiver is configured to send a plurality of types of transmission waves; and
wherein a type of the transmission wave to be used for the measurement is changed in association with a change of a polishing condition by said polish controller.

14. The substrate peripheral portion polishing apparatus of claim 1,
wherein said polish controller is configured to control a polishing of the substrate based on the polished state and a control parameter of a peripheral portion polishing tool.

15. The substrate peripheral portion polishing apparatus of claim 14,
wherein said polish controller is configured to interchange control based on the control parameter and the polished state, in accordance with progress of a polishing procedure of the substrate.

16. The substrate peripheral portion polishing apparatus of claim 1,
wherein said signal processing controller is configured to detect a polish end point by comparing a polish end point target set according to the reflected wave at an initial polishing stage and the reflected wave obtained from said wave transceiver.

17. The substrate peripheral portion polishing apparatus of claim 1, further comprising:
an end time setting unit for setting a polish end time at which a polish end point is reached, said end time setting unit being configured to set the polish end time based on a reference time until a predetermined reference polishing state is obtained in the polishing procedure.

18. The substrate peripheral portion polishing apparatus of claim 1, further comprising a substrate turning unit for turning the substrate.

19. The substrate peripheral portion polishing apparatus of claim 1, further comprising:
an abnormality detecting unit for determining whether a polish abnormality has occurred when a polish end point is not detected even if an actual polishing time reaches a predetermined maximum polishing time;
wherein said polish controller is configured to stop a polishing procedure when the polish abnormality is detected by said abnormality detecting unit.

* * * * *